United States Patent
Greenfield et al.

(10) Patent No.: US 10,954,306 B2
(45) Date of Patent: Mar. 23, 2021

(54) ANTIBODY THAT RECOGNISES THE T14 PEPTIDE OF ACHE

(71) Applicant: Neuro-Bio Ltd, Abingdon (GB)

(72) Inventors: Susan Adele Greenfield, Abingdon (GB); Sara Garcia-Rates, Abingdon (GB); Paul Morrill, Abingdon (GB)

(73) Assignee: NEURO-BIO LTD, Abingdon (GB)

( * ) Notice: Subject to any disclaimer, the term of this patent is extended or adjusted under 35 U.S.C. 154(b) by 0 days.

(21) Appl. No.: 15/561,021

(22) PCT Filed: Mar. 23, 2016

(86) PCT No.: PCT/GB2016/050804
§ 371 (c)(1),
(2) Date: Sep. 22, 2017

(87) PCT Pub. No.: WO2016/156803
PCT Pub. Date: Oct. 6, 2016

(65) Prior Publication Data
US 2018/0051094 A1 Feb. 22, 2018

(30) Foreign Application Priority Data

Mar. 27, 2015 (GB) .................................... 1505239
Jan. 18, 2016 (GB) .................................... 1600871

(51) Int. Cl.
C07K 16/40 (2006.01)

(52) U.S. Cl.
CPC .......... *C07K 16/40* (2013.01); *C07K 2317/33* (2013.01); *C07K 2317/34* (2013.01); *G01N 2500/10* (2013.01); *G01N 2800/28* (2013.01); *G01N 2800/2821* (2013.01)

(58) Field of Classification Search
CPC ............... C07K 16/40; C07K 2317/33; C07K 2317/34; G01N 2800/28; G01N 2500/10; G01N 2800/2821; G01N 21/00; A61P 43/00; A61P 25/28; A61P 25/16; A61P 25/14; A61P 25/02; A61P 21/00
See application file for complete search history.

(56) References Cited

FOREIGN PATENT DOCUMENTS

| WO | WO 97/35962 A1 | 10/1997 |
| WO | WO 1997/035962 | * 10/1997 |
| WO | WO 01/73446 A1 | 10/2001 |

OTHER PUBLICATIONS

Zimmermann M., British J of Pharmacology, 170:953-967, 2013.*
International Search Report and Written Opinion in PCT/GB2016/050804 dated May 27, 2016, 15 pages.
Cottingham, M. et al., The Intact Human Acetylcholinesterase C-Terminal Oligomerization Domain Is α-Helical In Situ and in Isolation, but a Shorter Fragment Forms β-Sheet-Rich Amyloid Fibrils and Protofibrillar Oligomers (2003) *Biochemistry* 42:10863-10873.
Greenfield, S. et al., Discovering and targeting the basic mechanism of neurodegeneration: The role of peptides from the C-terminus of acetylcholinesterase Non-hydrolytic effects of ache: The actions of peptides derived from the C-terminal and their relevance to neurodegeneration (2013) *Chemico-Biological Interactions* 203:543-546.
Halliday, A. et al., Evaluation of a technique to identify acetylcholinesterase C-terminal peptides in human serum samples (2010) *Chemico-Biological Interactions* 187:110-114.
Jean L. et al., Heterologous Amyloid Seeding: Revisiting the Role of Acetylcholinesterase in Alzheimer's Disease (2001) PL0S ONE 2(7):E652-E654.
Vijayan, R. et al., Conformational Preferences of a 14-Residue Fibrillogenic Peptide from Acetylcholinesterase (2010) *Biochemistry* 49:3678-3684.

* cited by examiner

*Primary Examiner* — Kimberly Ballard
*Assistant Examiner* — Stacey N MacFarlane
(74) *Attorney, Agent, or Firm* — Squire Patton Boggs (US) LLP

(57) ABSTRACT

The invention relates to antibodies, and in particular, to antibodies used in the diagnosis and treatment of neurodegenerative disorders, such as Alzheimer's disease and Parkinson's disease. The invention extends to methods of diagnosis and therapy of neurodegenerative disorders, and to assays and screens for isolating novel therapeutic compounds for treating such diseases.

6 Claims, 18 Drawing Sheets
Specification includes a Sequence Listing.

SEQUENCE LISTING

```
<160> NUMBER OF SEQ ID NOS: 31

<210> SEQ ID NO 1
<211> LENGTH: 614
<212> TYPE: PRT
<213> ORGANISM: Homo sapiens

<400> SEQUENCE: 1

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Thr Ser Pro Thr Pro
    130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
        195                 200                 205

Leu Ala Leu Gln Trp Val Gln Glu Asn Val Ala Ala Phe Gly Gly Asp
    210                 215                 220
```

-continued

```
Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
            245                 250                 255

Val Leu Gln Ser Gly Ala Pro Asn Gly Pro Trp Ala Thr Val Gly Met
        260                 265                 270

Gly Glu Ala Arg Arg Ala Thr Gln Leu Ala His Leu Val Gly Cys
    275                 280                 285

Pro Pro Gly Gly Thr Gly Gly Asn Asp Thr Glu Leu Val Ala Cys Leu
290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
                325                 330                 335

Asp Phe Leu Ser Asp Thr Pro Glu Ala Leu Ile Asn Ala Gly Asp Phe
            340                 345                 350

His Gly Leu Gln Val Leu Val Gly Val Val Lys Asp Glu Gly Ser Tyr
        355                 360                 365

Phe Leu Val Tyr Gly Ala Pro Gly Phe Ser Lys Asp Asn Glu Ser Leu
    370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
            420                 425                 430

Val Gly Asp His Asn Val Val Cys Pro Val Ala Gln Leu Ala Gly Arg
        435                 440                 445

Leu Ala Ala Gln Gly Ala Arg Val Tyr Ala Tyr Val Phe Glu His Arg
    450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
                485                 490                 495

Thr Ala Glu Glu Lys Ile Phe Ala Gln Arg Leu Met Arg Tyr Trp Ala
            500                 505                 510

Asn Phe Ala Arg Thr Gly Asp Pro Asn Glu Pro Arg Asp Pro Lys Ala
        515                 520                 525

Pro Gln Trp Pro Pro Tyr Thr Ala Gly Ala Gln Tyr Val Ser Leu
    530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Asp Thr
                565                 570                 575

Leu Asp Glu Ala Glu Arg Gln Trp Lys Ala Glu Phe His Arg Trp Ser
            580                 585                 590

Ser Tyr Met Val His Trp Lys Asn Gln Phe Asp His Tyr Ser Lys Gln
        595                 600                 605

Asp Arg Cys Ser Asp Leu
    610
```

<210> SEQ ID NO 2
<211> LENGTH: 30
<212> TYPE: PRT

<213> ORGANISM: Homo sapiens

<400> SEQUENCE: 2

Lys Ala Glu Phe His Arg Trp Ser Ser Tyr Met Val His Trp Lys Asn
1               5                   10                  15

Gln Phe Asp His Tyr Ser Lys Gln Asp Arg Cys Ser Asp Leu
            20                  25                  30

<210> SEQ ID NO 3
<211> LENGTH: 14
<212> TYPE: PRT
<213> ORGANISM: Homo sapiens

<400> SEQUENCE: 3

Ala Glu Phe His Arg Trp Ser Ser Tyr Met Val His Trp Lys
1               5                   10

<210> SEQ ID NO 4
<211> LENGTH: 15
<212> TYPE: PRT
<213> ORGANISM: Homo sapiens

<400> SEQUENCE: 4

Asn Gln Phe Asp His Tyr Ser Lys Gln Asp Arg Cys Ser Asp Leu
1               5                   10                  15

<210> SEQ ID NO 5
<211> LENGTH: 15
<212> TYPE: PRT
<213> ORGANISM: Homo sapiens

<400> SEQUENCE: 5

Asn Gln Phe Asp His Tyr Ser Lys Gln Asp Arg Cys Ser Asp Leu
1               5                   10                  15

<210> SEQ ID NO 6
<211> LENGTH: 4
<212> TYPE: PRT
<213> ORGANISM: Homo sapiens

<400> SEQUENCE: 6

Val His Trp Lys
1

<210> SEQ ID NO 7
<211> LENGTH: 15
<212> TYPE: PRT
<213> ORGANISM: Artificial Sequence
<220> FEATURE:
<223> OTHER INFORMATION: Keyhole Limpet Hemocyanin (KLH) protein
      cross-linked to the T14 protein (SEQ ID No:3)

<400> SEQUENCE: 7

Cys Ala Glu Phe His Arg Trp Ser Ser Tyr Met Val His Trp Lys
1               5                   10                  15

<210> SEQ ID NO 8
<211> LENGTH: 42
<212> TYPE: PRT
<213> ORGANISM: Homo sapiens

<400> SEQUENCE: 8

Asp Ala Glu Phe Arg His Asp Ser Gly Tyr Glu Val His His Gln Lys
1               5                   10                  15

```
Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

<210> SEQ ID NO 9

<400> SEQUENCE: 9

000

<210> SEQ ID NO 10
<211> LENGTH: 9
<212> TYPE: PRT
<213> ORGANISM: Homo sapiens

<400> SEQUENCE: 10

```
Trp Ser Ser Tyr Met Val His Trp Lys
1               5
```

<210> SEQ ID NO 11
<211> LENGTH: 10
<212> TYPE: PRT
<213> ORGANISM: Homo sapiens

<400> SEQUENCE: 11

```
Arg Trp Ser Ser Tyr Met Val His Trp Lys
1               5                   10
```

<210> SEQ ID NO 12
<211> LENGTH: 11
<212> TYPE: PRT
<213> ORGANISM: Homo sapiens

<400> SEQUENCE: 12

```
His Arg Trp Ser Ser Tyr Met Val His Trp Lys
1               5                   10
```

<210> SEQ ID NO 13
<211> LENGTH: 12
<212> TYPE: PRT
<213> ORGANISM: Homo sapiens

<400> SEQUENCE: 13

```
Phe His Arg Trp Ser Ser Tyr Met Val His Trp Lys
1               5                   10
```

<210> SEQ ID NO 14
<211> LENGTH: 13
<212> TYPE: PRT
<213> ORGANISM: Homo sapiens

<400> SEQUENCE: 14

```
Glu Phe His Arg Trp Ser Ser Tyr Met Val His Trp Lys
1               5                   10
```

<210> SEQ ID NO 15
<211> LENGTH: 14
<212> TYPE: PRT
<213> ORGANISM: Homo sapiens

<400> SEQUENCE: 15

```
Ala Glu Phe His Arg Trp Ser Ser Tyr Met Val His Trp Lys
1               5                   10
```

```
<210> SEQ ID NO 16
<211> LENGTH: 9
<212> TYPE: PRT
<213> ORGANISM: Homo sapiens

<400> SEQUENCE: 16

Arg Trp Ser Ser Tyr Met Val His Trp
1               5

<210> SEQ ID NO 17
<211> LENGTH: 10
<212> TYPE: PRT
<213> ORGANISM: Homo sapiens

<400> SEQUENCE: 17

His Arg Trp Ser Ser Tyr Met Val His Trp
1               5                   10

<210> SEQ ID NO 18
<211> LENGTH: 11
<212> TYPE: PRT
<213> ORGANISM: Homo sapiens

<400> SEQUENCE: 18

Phe His Arg Trp Ser Ser Tyr Met Val His Trp
1               5                   10

<210> SEQ ID NO 19
<211> LENGTH: 12
<212> TYPE: PRT
<213> ORGANISM: Homo sapiens

<400> SEQUENCE: 19

Glu Phe His Arg Trp Ser Ser Tyr Met Val His Trp
1               5                   10

<210> SEQ ID NO 20
<211> LENGTH: 13
<212> TYPE: PRT
<213> ORGANISM: Homo sapiens

<400> SEQUENCE: 20

Ala Glu Phe His Arg Trp Ser Ser Tyr Met Val His Trp
1               5                   10

<210> SEQ ID NO 21
<211> LENGTH: 14
<212> TYPE: PRT
<213> ORGANISM: Homo sapiens

<400> SEQUENCE: 21

Lys Ala Glu Phe His Arg Trp Ser Ser Tyr Met Val His Trp
1               5                   10

<210> SEQ ID NO 22
<211> LENGTH: 11
<212> TYPE: PRT
<213> ORGANISM: Homo sapiens

<400> SEQUENCE: 22

Arg Trp Ser Ser Tyr Met Val His Trp Lys Ala
1               5                   10

<210> SEQ ID NO 23
```

```
<211> LENGTH: 11
<212> TYPE: PRT
<213> ORGANISM: Homo sapiens

<400> SEQUENCE: 23

Trp Ser Ser Tyr Met Val His Trp Lys Ala Glu
1               5                   10

<210> SEQ ID NO 24
<211> LENGTH: 11
<212> TYPE: PRT
<213> ORGANISM: Homo sapiens

<400> SEQUENCE: 24

Ser Ser Tyr Met Val His Trp Lys Ala Glu Phe
1               5                   10

<210> SEQ ID NO 25
<211> LENGTH: 12
<212> TYPE: PRT
<213> ORGANISM: Homo sapiens

<400> SEQUENCE: 25

His Arg Trp Ser Ser Tyr Met Val His Trp Lys Ala
1               5                   10

<210> SEQ ID NO 26
<211> LENGTH: 12
<212> TYPE: PRT
<213> ORGANISM: Homo sapiens

<400> SEQUENCE: 26

Arg Trp Ser Ser Tyr Met Val His Trp Lys Ala Glu
1               5                   10

<210> SEQ ID NO 27
<211> LENGTH: 12
<212> TYPE: PRT
<213> ORGANISM: Homo sapiens

<400> SEQUENCE: 27

Trp Ser Ser Tyr Met Val His Trp Lys Ala Glu Phe
1               5                   10

<210> SEQ ID NO 28
<211> LENGTH: 13
<212> TYPE: PRT
<213> ORGANISM: Homo sapiens

<400> SEQUENCE: 28

Phe His Arg Trp Ser Ser Tyr Met Val His Trp Lys Ala
1               5                   10

<210> SEQ ID NO 29
<211> LENGTH: 13
<212> TYPE: PRT
<213> ORGANISM: Homo sapiens

<400> SEQUENCE: 29

Arg Trp Ser Ser Tyr Met Val His Trp Lys Ala Glu Phe
1               5                   10

<210> SEQ ID NO 30
<211> LENGTH: 14
<212> TYPE: PRT
```

```
<213> ORGANISM: Homo sapiens

<400> SEQUENCE: 30

Glu Phe His Arg Trp Ser Ser Tyr Met Val His Trp Lys Ala
1               5                   10

<210> SEQ ID NO 31
<211> LENGTH: 14
<212> TYPE: PRT
<213> ORGANISM: Homo sapiens

<400> SEQUENCE: 31

His Arg Trp Ser Ser Tyr Met Val His Trp Lys Ala Glu Phe
1               5                   10
```

ANTIBODY THAT RECOGNISES THE T14 PEPTIDE OF ACHE

CROSS-REFERENCE TO RELATED APPLICATIONS

This application is a national stage of international application no. PCT/GB2016/050804, filed 23 Mar. 2016, which claims the benefit of Great Britain application no. 1505239.2, filed 27 Mar. 2015, and of Great Britain application no. 1600871.6, filed 18 Jan. 2016, the contents of each of which are hereby incorporated by reference in their entireties.

The invention relates to antibodies, and in particular, to antibodies used in the diagnosis and treatment of neurodegenerative disorders, such as Alzheimer's disease and Parkinson's disease. The invention extends to methods of diagnosis and therapy of neurodegenerative disorders, and to assays and screens for isolating novel therapeutic compounds for treating such diseases.

Alzheimer's disease primarily affects men and women over the age of 65 and the likelihood of being diagnosed with the disease increases substantially with age. With the percentage of adults over the age of 65 expected to grow worldwide over the next 40 years, the incidence of Alzheimer's disease is expected to more than double, escalating from 21 million cases in 2010 to 53 million in 2050 (statistics from www.alzheimersresearchuk.org and www.alz.org). This exponential increase in the expected number of patients presenting with Alzheimer's disease not only represents a major area of unmet medical need, but offers a significant market opportunity for therapeutics and diagnostics as there is currently no fully effective method of treating the disease.

There has been no new drug to combat Alzheimer's disease specifically, nor neurodegeneration more generally, in the last 10 years. The reason is that as yet, the basic underlying brain mechanism has not yet been identified that could consequently be targeted pharmaceutically. The main contender for accounting for the process of neurodegeneration is the 'amyloid hypothesis', where neuronal death is attributed to disruption of the cell membrane by toxic deposits of amyloid, characteristic of post-mortem Alzheimer brain, and resulting from abnormal cleavage of amyloid precursor protein. However, this 'amyloid hypothesis' does not explain the co-pathology frequently observed with Alzheimer's and Parkinson's diseases, nor the characteristic selectivity of cells vulnerable to degeneration despite the potential ubiquity of amyloid in all brain cells, nor the absence of amyloid deposits in animal models of dementia, nor indeed the occurrence of amyloid in certain brain regions where cognitive deficits are not apparent. Despite the popularity of amyloid formation as a pharmaceutical target over the last two decades, no treatment based on this theory has as yet proved effective. A more likely possibility is that once the neurodegenerative process is underway, then amyloid will additionally be generated as a secondary, exacerbating effect that is less specific.

One clue for identifying the primary mechanism of neurodegeneration, could be that only various neuronal groups are primarily vulnerable. Moreover, the diverse cell sub-groups prone to Alzheimer's, Parkinson's and Motor Neurone Diseases nonetheless are adjacent to each other and form a continuous 'hub' extending from brainstem to forebrain that all send diffuse projections upwards and outwards to higher cerebral centres. Hence, despite their heterogeneity in transmitters, these neuronal groups have been collectively dubbed 'Global' neurons to distinguish them from the more familiar and localised circuits of cells in most other parts of the brain, such as cerebellum, thalamus, cortex etc. These selectively vulnerable Global neurons were previously identified, albeit using a different terminology ('isodendritic core') as pivotal in neurodegeneration several decades ago.

The sub-groups of Global neurons have a specific feature in common that might explain the puzzling and as yet unanswered question as to why only these cells succumb to progressive death whilst their counterparts elsewhere in the brain, even when damaged by stroke, do not: they retain a robust plasticity into and throughout adulthood, accompanied by a specific sensitivity to substances aiding and sustaining growth—'trophic factors'. In the developing brain, trophic factors work by stimulating calcium influx, which triggers a cascade of events within the cell, eventually resulting in selective differentiation and growth. However, in higher doses or with longer exposures, sustained calcium entry can be toxic to neurons. Most significantly, a further determining factor in whether or not calcium entry triggers trophic or toxic effects, is age: as neurons mature, an erstwhile trophic level of intracellular calcium becomes lethal.

The inventors have previously proposed that the neurodegenerative process is in fact an aberrantly activated process of development. In support of this hypothesis, a hypertrophy of the brainstem 'hub' neurons has actually been reported in Alzheimer brains (Bowser et al., 1997, Brain Pathol. 7: 723-30). If large areas of this hub are damaged, then more than one neurodegenerative disease will present, as occurs in the frequently seen but never as yet explained cases of co-pathology with Alzheimer's and Parkinson's diseases. Interestingly, all the neurons within the vulnerable hub of Global neurons, despite transmitter heterogeneity, all contain the familiar enzyme acetylcholinesterase (AChE). AChE is therefore present in neurons where it would be unable to perform its normal function, since such sub-groups of cells as the noradrenergic locus coeruleus, the dopaminergic substantia nigra, or the serotonergic raphe nuclei, in no cases contain the usual substrate, acetylcholine. A further unexpected deviation from its normal, enzymatic role is that the AChE is actually released from Global neurons, presumably as some kind of inter-cellular messenger in its own right. In general, AChE is now widely and well-established as a signalling molecule that has trophic activity in a diverse variety of situations in both neural and non-neural tissue.

The inventors have previously shown that AChE, operating as a trophic agent independent of its enzymatic action, does indeed trigger calcium entry into neurons. It is possible therefore that within Global neurons, AChE has a dual non-classical action that ranges along a trophic-toxic axis, depending on amount, duration of availability and, most significantly, age. If standard neurons are damaged in adulthood, as in a stroke, others will compensate functionally. In contrast, Global neurons will respond by calling on their trophic resources in an attempt to regenerate. But because the subsequent calcium influx will be lethal in the older, mature cells, the resulting damage will trigger further attempts to compensate in a pernicious cycle that characterises neurodegeneration.

Acetylcholinesterase (AChE) is expressed at different stages of development in various forms, all of which have identical enzymatic activity, but which have very different molecular composition. The 'tailed' (T-AChE) is expressed at synapses and the inventors have previously identified two peptides that could be cleaved from the C-terminus, one referred to as "T14", within the other which is known as "T30", and which both have strong sequence homology to the comparable region of β-amyloid. The AChE C-terminal peptide "T14'" has been identified as being the salient part of the AChE molecule responsible for its range of non-hydrolytic actions. The synthetic 14 amino acids peptide analogue (i.e. "T14"), and subsequently the larger, more stable, and more potent amino acid sequence in which it is embedded (i.e. "T30") display actions comparable to those reported for 'non-cholinergic' AChE, whereas the inert residue within the T30 sequence (i.e. "T15") is without effect.

Acute effects of T14 and T30 are that they:— (i) modulate calcium entry into neurons in brain slices over time scales from milliseconds to hours; (ii) compromise cell viability in PC 12 cells and also in neuronal organotypic cultures in vitro; (iii) modulate 'compensatory' calcium-induced AChE release from neurons and PC 12 cells; (iv) activate calcium currents in oocytes and neurons in brain slices; (v) synergise with amyloid in toxic effects; and (vi) are involved in amyloid precursor protein production and amyloid beta (Aβ) peptide release. Chronic effects of T14 and T30 are that they:— (i) reduce neuron growth; (ii) induce apoptosis; (iii) increase AChE release; (iv) bind to and modulate α7 nicotinic-receptor; and (v) enhance expression of the α7 receptor on the cell surface over 24 hours, thereby providing a feedforward mechanism for further toxicity.

Since T14 and T30 are more selective than β-amyloid in inducing toxicity and are also synergistic with amyloid exacerbating toxicity, it has been postulated that any agent which blocks the toxic effects of T14 or T30 would also reduce the less selective and subsequent toxic effect of amyloid.

As discussed in the Examples, the inventors have now isolated a novel antibody, which binds to the T14 peptide (SEQ ID No: 3) with high specificity, and which does not bind to the T30 peptide (SEQ ID No: 2) or to β-amyloid. Accordingly, this antibody will have significant utility in the diagnosis and therapy of neurodegenerative disorders, such as Alzheimer's disease or Parkinson's disease.

Therefore, according to a first aspect of the invention, there is provided an antibody or antigen-binding fragment thereof that specifically binds to SEQ ID No:3, or a variant or fragment thereof.

Advantageously, the data described in the Examples show that the antibody of the invention binds to the T14 peptide with very high specificity. Any antibody that binds to T30 would raise the risk of detecting an antigen that was in fact the inert component of the larger peptide, which should be avoided. However, the antibody according to the invention instead binds specifically to just T14, or variants or fragments thereof, and not to T30, and so one can be sure that its bioactive, toxic actions would be both isolated and blocked. The antibody is surprisingly viable in biological tissue, even tissue which has been deep frozen. Most surprising of all is that significant differences can be detected in Alzheimer's disease samples compared to control brains. Accordingly, these findings suggest that the antibody of the invention can be used as a diagnostic tool, as well as in therapeutic intervention.

Acetylcholinesterase is a serine protease that hydrolyses acetylcholine, and is well-known to the skilled person. The major form of acetylcholinesterase which is found in the brain is known as tailed acetylcholinesterase (T-AChE). The protein sequence of one embodiment of human tailed acetylcholinesterase (Gen Bank: AAA68151.1) is 614 amino acids in length, and is provided herein as SEQ ID No:1, as follows:

[SEQ ID No: 1]
```
  1  mrppqcllht pslaspllll llwllgggvg aegredaell vtvrggrlrg irlktpggpv
 61  saflgipfae ppmgprrflp pepkqpwsgv vdattfqsvc yqyvdtlypg fegtemwnpn
121  relsedclyl nvwtpyprpt sptpvlwiy  gggfysgass ldvydgrflv qaertvlvsm
181  nyrvgafgfl alpgsreapg nvglldqrla lqwvqenvaa fggdptsvtl fgesagaasv
241  gmhllsppsr glfhravlqs gapngpwatv gmgearrrat qlahlvgcpp ggtggndtel
301  vaclrtrpaq vlvnhewhvl pqesvfrfsf vpvvdgdfls dtpealinag dfhglqvlvg
361  vvkdegsyfl vygapgfskd neslisraef lagvrvgvpq vsdlaaeavv lhytdwlhpe
421  dparlreals dvvgdhnvvc pvaqlagrla aqgarvyayv fehrastlsw plwmgvphgy
481  eiefifgipl dpsrnytaee kifaqrlmry wanfartgdp neprdpkapq wppytagaqq
541  yvsldlrple vrrglraqac afwnrflpkl lsatdtldea erqwkaefhr wssymvhwkn
601  qfdhyskqdr csdl
```

The amino acid sequence of T30 (which corresponds to the last 30 amino acid residues of SEQ ID No:1) is provided herein as SEQ ID No:2, as follows:—

[SEQ ID No: 2]
KAEFHRWSSYMVHWKNQFDHYSKQDRCSDL

Preferably, the antibody or antigen-binding fragment thereof does not bind to SEQ ID No:2. As discussed above, by developing an antibody that targets T30, there would be the risk of detecting an antigen that was in fact the inert component of the larger peptide. However, advantageously the antibody of the invention instead binds specifically to T14, and so one can be sure that it would both isolate and block the bioactive, toxic actions of only T14.

The amino acid sequence of T14 (which corresponds to the 14 amino acid residues located towards the end of SEQ ID No:1, and lacks the final 15 amino acids found in T30) is provided herein as SEQ ID No:3, as follows:—

[SEQ ID No: 3]
AEFHRWSSYMVHWK

The amino acid sequence of T15 (which corresponds to the last 15 amino acid residues of SEQ ID No:1) is provided herein as SEQ ID No:4, as follows:—

```
                                          [SEQ ID No: 4]
NQFDHYSKQDRCSDL
```

Preferably, the antibody or antigen-binding fragment thereof does not bind to SEQ ID No:4. T15 is the inert component of T30, and as such, serves as an appropriate control for the antibody's selectivity of T14.

The amino acid sequence of part of β-amyloid (Aβ) is provided herein as SEQ ID No:8, as follows:—

```
                                          [SEQ ID No: 8]
DAEFRHDSGYEVHHQKLVFFAEDVGSNKGAIIGLMVGGVVIA
```

Preferably, the antibody or antigen-binding fragment thereof does not bind to SEQ ID No:8.

The invention extends to both whole antibodies (i.e. immunoglobulins) with immunospecificity for a SEQ ID No:3, as well as to antigen-binding fragments or regions of the corresponding full-length antibody.

The antibody or antigen-binding fragment thereof may be monovalent, divalent or polyvalent. Monovalent antibodies are dimers (HL) comprising a heavy (H) chain associated by a disulphide bridge with a light chain (L). Divalent antibodies are tetramer (H2L2) comprising two dimers associated by at least one disulphide bridge. Polyvalent antibodies may also be produced, for example by linking multiple dimers. The basic structure of an antibody molecule consists of two identical light chains and two identical heavy chains which associate non-covalently and can be linked by disulphide bonds. Each heavy and light chain contains an amino-terminal variable region of about 110 amino acids, and constant sequences in the remainder of the chain. The variable region includes several hypervariable regions, or Complementarity Determining Regions (CDRs), that form the antigen-binding site of the antibody molecule and determine its specificity for the antigen, i.e. SEQ ID No:3, or variant or fragment thereof (e.g. an epitope). On either side of the CDRs of the heavy and light chains is a framework region, a relatively conserved sequence of amino acids that anchors and orients the CDRs. Antibody fragments may include a bi-specific antibody (BsAb) or a chimeric antigen receptor (CAR).

The constant region consists of one of five heavy chain sequences (μ, γ, ζ, α, or ε) and one of two light chain sequences (κ or λ). The heavy chain constant region sequences determine the isotype of the antibody and the effector functions of the molecule.

Preferably, the antibody or antigen-binding fragment thereof is isolated or purified.

In one preferred embodiment, the antibody or antigen-binding fragment thereof comprises a polyclonal antibody, or an antigen-binding fragment thereof. The antibody or antigen-binding to fragment thereof may be generated in a rabbit, mouse or rat.

As described in the Examples, the inventors have prepared a highly specific polyclonal antibody from rabbit. Preferably, the antibody or antigen-binding fragment thereof is obtained by immunising a host animal with SEQ ID No:3, or a variant or fragment thereof, and then collecting the antibody or antigen-binding fragment thereof. The host animal is most preferably a rabbit.

In another preferred embodiment, the antibody or antigen-binding fragment thereof comprises a monoclonal antibody or an antigen-binding fragment thereof. Preferably, the antibody of the invention is a human antibody. As used herein, the term "human antibody" can mean an antibody, such as a monoclonal antibody, which comprises substantially the same heavy and light chain CDR amino acid sequences as found in a particular human antibody exhibiting immunospecificity for SEQ ID No:3, or a variant or fragment thereof. An amino acid sequence, which is substantially the same as a heavy or light chain CDR, exhibits a considerable amount of sequence identity when compared to a reference sequence. Such identity is definitively known or recognizable as representing the amino acid sequence of the particular human antibody. Substantially the same heavy and light chain CDR amino acid sequence can have, for example, minor modifications or conservative substitutions of amino acids. Such a human antibody maintains its function of selectively binding to SEQ ID No:3 or a variant or fragment thereof.

The term "human monoclonal antibody" can include a monoclonal antibody with substantially or entirely human CDR amino acid sequences produced, for example by recombinant methods such as production by a phage library, by lymphocytes or by hybridoma cells.

The term "humanised antibody" can mean an antibody from a non-human species (e.g. mouse or rabbit) whose protein sequences have been modified to increase their similarity to antibodies produced naturally in humans.

The antibody may be a recombinant antibody. The term "recombinant human antibody" can include a human antibody produced using recombinant DNA technology.

The term "antigen-binding region" can mean a region of the antibody having specific binding to affinity for its target antigen, for example, the peptide of SEQ ID No:3, or a variant or fragment thereof. Preferably, the fragment is an epitope. The binding region may be a hypervariable CDR or a functional portion thereof. The term "functional portion" of a CDR can mean a sequence within the CDR which shows specific affinity for the target antigen. The functional portion of a CDR may comprise a ligand which specifically binds to SEQ ID No:3 or a fragment thereof.

The term "CDR" can mean a hypervariable region in the heavy and light variable chains. There may be one, two, three or more CDRs in each of the heavy and light chains of the antibody. Normally, there are at least three CDRs on each chain which, when configured together, form the antigen-binding site, i.e. the three-dimensional combining site with which the antigen binds or specifically reacts. It has however been postulated that there may be four CDRs in the heavy chains of some antibodies.

The definition of CDR also includes overlapping or subsets of amino acid residues when compared against each other. The exact residue numbers which encompass a particular CDR or a functional portion thereof will vary depending on the sequence and size of the CDR. Those skilled in the art can routinely determine which residues comprise a particular CDR given the variable region amino acid sequence of the antibody.

The term "functional fragment" of an antibody can mean a portion of the antibody which retains a functional activity. A functional activity can be, for example antigen binding activity or specificity. A functional activity can also be, for example, an effector function provided by an antibody constant region. The term "functional fragment" is also intended to include, for example, fragments produced by protease digestion or reduction of a human monoclonal antibody and by recombinant DNA methods known to those skilled in the art. Human monoclonal antibody functional fragments include, for example individual heavy or light chains and fragments thereof, such as VL, VH and Fd; monovalent fragments, such as Fv, Fab, and Fab'; bivalent fragments such as F(ab')$_2$; single chain Fv (scFv); and Fc fragments.

The term "VL fragment" can mean a fragment of the light chain of a human monoclonal antibody which includes all or part of the light chain variable region, including the CDRs. A VL fragment can further include light chain constant region sequences.

The term "VH fragment" can means a fragment of the heavy chain of a human monoclonal antibody which includes all or part of the heavy chain variable region, including the CDRs.

The term "Fd fragment" can mean the heavy chain variable region coupled to the first heavy chain constant region, i.e. VH and CH-1. The "Fd fragment" does not include the light chain, or the second and third constant regions of the heavy chain.

The term "Fv fragment" can mean a monovalent antigen-binding fragment of a human monoclonal antibody, including all or part of the variable regions of the heavy and light chains, and absent of the constant regions of the heavy and light chains. The variable regions of the heavy and light chains include, for example, the CDRs. For example, an Fv fragment includes all or part of the amino terminal variable region of about 110 amino acids of both the heavy and light chains.

The term "Fab fragment" can mean a monovalent antigen-binding fragment of a human monoclonal antibody that is larger than an Fv fragment. For example, a Fab fragment includes the variable regions, and all or part of the first constant domain of the heavy and light chains. Thus, a Fab fragment additionally includes, for example, amino acid residues from about 110 to about 220 of the heavy and light chains.

The term "Fab' fragment" can mean a monovalent antigen-binding fragment of a human monoclonal antibody that is larger than a Fab fragment. For example, a Fab' fragment includes all of the light chain, all of the variable region of the heavy chain, and all or part of the first and second constant domains of the heavy chain. For example, a Fab' fragment can additionally include some or all of amino acid residues 220 to 330 of the heavy chain.

The term "F(ab')$_2$ fragment" can mean a bivalent antigen-binding fragment of a human monoclonal antibody. An F(ab')$_2$ fragment includes, for example, all or part of the variable regions of two heavy chains- and two light chains, and can further include all or part of the first constant domains of two heavy chains and two light chains.

The term "single chain Fv (scFv)" can mean a fusion of the variable regions of the heavy (VH) and light chains (VL) connected with a short linker peptide.

The term "bispecific antibody (BsAb)" can mean a bispecific antibody comprising two scFv linked to each other by a shorter linked peptide.

One skilled in the art knows that the exact boundaries of a fragment of an antibody are not important, so long as the fragment maintains a functional activity. Using well-known recombinant methods, one skilled in the art can engineer a polynucleotide sequence to express a functional fragment with any endpoints desired for a particular application. A functional fragment of the antibody may comprise or consist of a fragment with substantially the same heavy and light chain variable regions as the human antibody.

Preferably, the antigen-binding fragment thereof, with respect to the first aspect of the invention, is SEQ ID No:3-specific or immunospecific for an epitope within SEQ ID No:3. The antigen-binding fragment thereof may comprise or consist of any of the fragments selected from a group consisting of VH, VL, Fd, Fv, Fab, Fab', scFv, F (ab')$_2$ and Fc fragment.

The antigen-binding fragment thereof may comprise or consist of any one of the antigen binding region sequences of the VL, any one of the antigen binding region sequences of the VH, or a combination of VL and VH antigen binding regions of a human antibody. The appropriate number and combination of VH and VL antigen binding region sequences may be determined by those skilled in the art depending on the desired affinity and specificity and the intended use of the antigen-binding fragment. Functional fragments or antigen-binding fragments of antibodies may be readily produced and isolated using methods well known to those skilled in the art. Such methods include, for example, proteolytic methods, recombinant methods and chemical synthesis. Proteolytic methods for the isolation of functional fragments comprise using human antibodies as a starting material. Enzymes suitable for proteolysis of human immunoglobulins may include, for example, papain, and pepsin. The appropriate enzyme may be readily chosen by one skilled in the art, depending on, for example, whether monovalent or bivalent fragments are required. For example, papain cleavage results in two monovalent Fab' fragments that bind antigen and an Fc fragment. Pepsin cleavage, for example, results in a bivalent F (ab') fragment. An F (ab')$_2$ fragment of the invention may be further reduced using, for example, DTT or 2-mercaptoethanol to produce two monovalent Fab' fragments.

Functional or antigen-binding fragments of antibodies produced by proteolysis may be purified by affinity and column chromatographic procedures. For example, undigested antibodies and Fc fragments may be removed by binding to protein A. Additionally, functional fragments may be purified by virtue of their charge and size, using, for example, ion exchange and gel filtration chromatography. Such methods are well known to those skilled in the art.

The antibody or antigen-binding fragment thereof may be produced by recombinant methodology. Preferably, one initially isolates a polynucleotide encoding desired regions of the antibody heavy and light chains. Such regions may include, for example, all or part of the variable region of the heavy and light chains. Preferably, such regions can particularly include the antigen binding regions of the heavy and light chains, preferably the antigen binding sites, most preferably the CDRs.

The polynucleotide encoding the antibody or antigen-binding fragment thereof according to the invention may be produced using methods known to those skilled in the art. The polynucleotide encoding the antibody or antigen-binding fragment thereof may be directly synthesized by methods of oligonucleotide synthesis known in the art. Alternatively, smaller fragments may be synthesized and joined to form a larger functional fragment using recombinant methods known in the art.

As used herein, the term "immunospecificity" can mean the binding region is capable of immunoreacting with SEQ ID No:3, or a variant or fragment thereof, by specifically binding therewith. The antibody or antigen-binding fragment thereof can selectively interact with an antigen (e.g. SEQ ID No:3 or a variant or fragment thereof) with an affinity constant of approximately $10^{-5}$ to $10^{-13}$ M$^{-1}$, preferably $10^{-6}$ to $10^{-9}$ M$^{-1}$, even more preferably, $10^{-10}$ to $10^{-12}$ M$^{-1}$. In the Materials and Methods section, details are provided explaining how antibody concentrations are determined.

The term "immunoreact" can mean the binding region is capable of eliciting an immune response upon binding with SEQ ID No:3, or an epitope thereof.

The term "epitope" can mean any region of an antigen with the ability to elicit, and combine with, a binding region of the antibody or antigen-binding fragment thereof.

Preferably, the antibody or antigen-binding fragment thereof according to the invention specifically binds to one or more amino acid in the C-terminus of SEQ ID No:3. Preferably, the antibody or antigen-binding fragment thereof according to the invention specifically binds to one or more amino acid in SEQ ID No. 5 (i.e. SYMVHWK, which are the C-terminal amino acids numbers 7-14 of SEQ ID No.3). Preferably, the antibody or antigen-binding fragment thereof specifically binds to a C-terminal lysine (K) residue in the epitope.

As described in the Examples, the inventors have surprisingly observed that the C-terminal amino acid sequence VHWK in SEQ ID No:3, which is described herein as SEQ ID No. 6 (i.e. the C-terminal amino acids numbers 10-14 of SEQ ID No.3) acts as an epitope for the antibody or antigen-binding fragment thereof according to the invention. Accordingly, more preferably the antibody or antigen-binding fragment thereof specifically binds to one or more amino acid in SEQ ID No.6. Most preferably, the antibody or antigen-binding fragment thereof specifically binds to SEQ ID No.6. Hence, it will be appreciated that the epitope to which the antibody binds comprises or consists of SEQ ID No.6.

The polyclonal antibody described herein proved to be highly specific to the T14 peptide, and especially the C-terminal sequence, —VHWK. Furthermore, its recognition of the full AChE protein suggests that this epitope sequence is exposed and accessible in the tertiary structure. The fact that the antibody did not recognise the linear T30 peptide fragment (within which T14 occurs) is believed to be due to the absence of an exposed lysine (K) at the C-terminal end of the T30 sequence.

Based on the discovery of the —VHWK epitope within the T14 peptide, the inventors believe that these sequences can be used as an antigen for the production of useful antibodies. As described in the Examples, the T14 peptide (SEQ ID No:3) was cysteine-crosslinked to Keyhole Limpet Hemocyanin (KLH) acting as a carrier protein which stimulates an immune response in the host. The KLH protein cross-linked to T14 is referred to herein as SEQ ID No:7.

Hence, in a second aspect, there is provided SEQ ID No:3 or SEQ ID No:7, or a variant or fragment thereof, for use as an antigen.

Preferably, the antigen acts as an epitope to which the antibody binds. Preferably, the variant or fragment comprises or consists of SEQ ID No:6.

In a third aspect, there is provided an antibody or antigen-binding fragment thereof obtained by a method comprising:—
  (i) immunising a host organism with SEQ ID No:3 or SEQ ID No:7, or a variant or fragment thereof; and
  (ii) collecting the antibody or antigen-binding fragment thereof from the host.

The host may be a mammal, and may be a human, rabbit or mouse. Preferably, the variant or fragment comprises or consists of SEQ ID No:6. Preferably, the method comprises bleeding the host animal, and then collecting the antibody or antigen-binding fragment thereof from the blood serum. Preferably, the serum is passed through a gravity column with covalently bound peptide-support. Following washing, the antibody or antigen-binding fragment thereof is preferably eluted in acidic buffer, and the solution may then be neutralized. The method may further comprise dialysis against a suitable buffer (e.g. PBS) and, optionally, lyophilisation.

Advantageously, the antibody or antigen-binding fragment thereof according to the first aspect of the invention, has utility of a therapeutic agent in its own right. However, in addition, technologies to maximize drug efficacy have been evaluated, including glycosylation engineering to enhance the ADCC (Antibody-Dependent Cell-Mediated Cytotoxicity) and/or CDC (Complement-Dependent Cytotoxicity) activity of the antibody or antigen-binding fragment thereof, conjugation to a cytotoxic moiety, such as radiation, a cytotoxic drug or toxin.

Thus, in a fourth aspect, there is provided an antibody-drug conjugate (ADC) comprising the antibody or antigen-binding fragment thereof of the first or third aspect, and a cytotoxic moiety.

Antibody-drug conjugates (ADC) can be used to deliver a potent cytotoxic drug selectively to a target cell via an antibody. One key parameter for ADC development is that the antibody may be capable of being endocytosed upon binding to the target antigen, i.e. SEQ ID No:3 or SEQ ID No:6. Therefore, endocytosed antibody may deliver the conjugated drug into target cells.

The cytotoxic moiety may be any toxin, such as one described in Antibody-Drug Conjugates and Immunotoxins: From Pre-Clinical Development to therapeutic applications (see page n8). Also specific examples of antibody therapy in AD are: SOLANEZUMAB (Lilly): www.alzforum.org/therapeutics/solanezumab GANTENERUMAB (Roche): www.alzforum.org/therapeutics/solanezumab Other examples (includes all the immunotherapy for Alzheimer's that are in Phase I to Phase III): www.alzforum.org/therapeutics/search?fda_statuses=&target_types %5B %5D=170&thera py_types %5B %5D=162&conditions %5B %5D=145&keywords-entry=&keywords=

The drug moiety may be an alpha-emitting radionucleotide, such as a 225Ac label. These toxins can be linked to the antibody or antigen-binding fragment thereof via a cleavable linker, such as a disulfide bond, a hydrazone linker or a peptide linker, or via a non-cleavable linkers, such as a thioether bond using a SMCC (N-succinimidyl-4-(N-maleimidomethyl)-cyclohexane-1-carboxylate) linker.

As described in the Examples, the antibody of the invention binds to the T14 peptide with very high specificity. The antibody is surprisingly viable in biological tissue, even tissue which has been deep frozen. The data also show that a T14-like peptide (i.e. SEQ ID No:3 or a variant or fragment thereof) exists as an independent biochemical entity which can be detected in patients suffering from, or predisposed to, a neurodegenerative disorder, such as Alzheimer's disease. Accordingly, these findings suggest that the antibody of the invention can be used as a diagnostic tool, as well as in therapeutic intervention for treating a neurodegenerative disorder.

Therefore, according to a fifth aspect, there is provided an antibody or an antigen-binding fragment thereof according to the first or third aspect, or an antibody-drug conjugate according to the fourth aspect, each being optionally derivatised, for use in therapy or in diagnosis.

The antibody or antigen-binding fragment thereof, or the antibody-drug conjugate may be used in the treatment, amelioration or prevention of neurodegenerative disorder.

Therefore, according to a sixth aspect, there is provided an antibody or an antigen-binding fragment thereof according to the first or third aspect, or an antibody-drug conjugate according to the fourth aspect, each being optionally derivatised, for use in treating, preventing or ameliorating neurodegenerative disorder.

According to a seventh aspect, there is provided a method of treating, preventing or ameliorating neurodegenerative disorder in a subject, the method comprising administering, to a patient in need of such treatment, a therapeutically effective amount of an antibody or a antigen-binding fragment thereof according to the first or third aspect, or an antibody-drug conjugate according to the fourth aspect, each being optionally derivatised.

The term "derivatised" can mean that the antibody or antigen-binding fragment thereof, or conjugate may be modified prior to use, preferably to produce a derivative or variant thereof. Examples of derivatisation may include PEGylated antibodies or PEGylated antibody fragments, or antibody-cytokine fusion proteins. However, in some embodiments, the antibody or antigen-binding fragment thereof or conjugate may not be derivatised.

Preferably, the neurodegenerative disorder is selected from a group consisting of Alzheimer's disease; Parkinson's disease; Huntington's disease; Motor Neurone disease; Spinocerebellar type 1, type 2, and type 3; Amyotrophic Lateral Sclerosis (ALS); and Frontotemporal Dementia. Most preferably, the neurodegenerative disorder is Alzheimer's disease.

It will be appreciated that antibodies, fragments thereof, and conjugates according to the invention (collectively referred to herein as "agents") may be used in a monotherapy (e.g. the use of an antibody or antigen binding fragment thereof alone, or the use of the antibody-drug conjugate alone), for treating, ameliorating or preventing neurodegenerative disorder.

Alternatively, agents according to the invention may be used as an adjunct to, or in combination with, known therapies for treating, ameliorating, or preventing neurodegenerative disorder, such as such as other acetylcholinesterase inhibitors.

The agents according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given, and preferably enables delivery of the agents across the blood-brain barrier.

Medicaments comprising agents of the invention may be used in a number of ways. For instance, oral administration may be required, in which case the agents may be contained within a composition that may, for example, be ingested orally in the form of a tablet, capsule or liquid. Compositions comprising agents and medicaments of the invention may be administered by inhalation (e.g. intranasally). Compositions may also be formulated for topical use. For instance, creams or ointments may be applied to the skin, for example adjacent to the brain.

Agents and medicaments according to the invention may also be incorporated within a slow- or delayed-release device. Such devices may, for example, be inserted on or under the skin, and the medicament may be released over weeks or even months. The device may be located at least adjacent the treatment site, i.e. the brain. Such devices may be particularly advantageous when long-term treatment with agents used according to the invention is required and which would normally require frequent administration (e.g. at least daily injection).

In a preferred embodiment, agents and medicaments according to the invention may be administered to a subject by injection into the blood stream or directly into a site requiring treatment. For example, the medicament may be injected at least adjacent the brain. Injections may be intravenous (bolus or infusion) or subcutaneous (bolus or infusion), or intradermal (bolus or infusion).

It will be appreciated that the amount of the antibodies, fragments, and conjugate (i.e. agent) that is required is determined by its biological activity and bioavailability, which in turn depends on the mode of administration, the physiochemical properties of the agent, and whether it is being used as a monotherapy or in a combined therapy. The frequency of administration will also be influenced by the half-life of the agent within the subject being treated. Optimal dosages to be administered may be determined by those skilled in the art, and will vary with the particular agent in use, the strength of the pharmaceutical composition, the mode of administration, and the advancement of the bacterial infection. Additional factors depending on the particular subject being treated will result in a need to adjust dosages, including subject age, weight, gender, diet, and time of administration.

Generally, a daily dose of between 0.001 µg/kg of body weight and 10 mg/kg of body weight of agent according to the invention may be used for treating, ameliorating, or preventing neurodegenerative disorder, depending upon which agent. More preferably, the daily dose of agent is between 0.01 µg/kg of body weight and 1 mg/kg of body weight, more preferably between 0.1 µg/kg and 100 µg/kg body weight, and most preferably between approximately 0.1 µg/kg and 10 µg/kg body weight.

The agent may be administered before, during or after onset of neurodegenerative disorder. Daily doses may be given as a single administration (e.g. a single daily injection). Alternatively, the agent may require administration twice or more times during a day. As an example, agents may be administered as two (or more depending upon the severity of the neurodegenerative disorder being treated) daily doses of between 0.07 µg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of agents according to the invention to a patient without the need to administer repeated doses. Known procedures, such as those conventionally employed by the pharmaceutical industry (e.g. in vivo experimentation, clinical trials, etc.), may be used to form specific formulations of the agents according to the invention and precise therapeutic regimes (such as daily doses of the agents and the frequency of administration).

In an eighth aspect of the invention, there is provided a pharmaceutical composition comprising an antibody or antigen-binding fragment thereof according to the first or third aspect, or an antibody-drug conjugate according to the fourth aspect, each being optionally derivatised; and optionally a pharmaceutically acceptable vehicle.

The pharmaceutical composition is preferably an anti-neurodegenerative disease composition, i.e. a pharmaceutical formulation used in the therapeutic amelioration, prevention or treatment of a neurodegenerative disorder in a subject, such as Alzheimer's disease.

The antibody or a functional fragment thereof, peptide or a nucleic acid may not be derivatised.

The invention also provides in a ninth aspect, a process for making the pharmaceutical composition according to the eighth aspect, the process comprising combining a therapeutically effective amount of an antibody or antigen-binding fragment thereof as defined in the first or third aspect, or an antibody-drug conjugate as defined in the fourth aspect, each being optionally derivatised, with a pharmaceutically acceptable vehicle.

The antibody or antigen-binding fragment thereof may be as defined with respect to the first aspect.

A "subject" may be a vertebrate, mammal, or domestic animal. Hence, medicaments according to the invention may be used to treat any mammal, for example livestock (e.g. a horse), pets, or may be used in other veterinary applications. Most preferably, the subject is a human being.

A "therapeutically effective amount" of the antibody or antigen-binding fragment thereof is any amount which, when administered to a subject, is the amount of agent that is needed to treat the neurodegenerative disease, or produce the desired effect.

For example, the therapeutically effective amount of antibody or fragment thereof used may be from about 0.001 ng to about 1 mg, and preferably from about 0.01 ng to about 100 ng. It is preferred that the amount of antibody or fragment is an amount from about 0.1 ng to about 10 ng, and most preferably from about 0.5 ng to about 5 ng.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The agent may be prepared as a sterile solid composition that may be dissolved or suspended at the time of administration using sterile water, saline, or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agents used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

As discussed herein, the antibody of the invention is highly specific or selective to the T14 peptide (i.e. SEQ ID No:3), and in particular the C-terminal sequence, —VHWK (i.e. SEQ ID No:6), which acts as the epitope. The antibody is surprisingly viable in biological tissue, even that which has been deep frozen. Furthermore, the data show that a T14-like peptide exists as an independent biochemical entity. These findings suggest that the detectable sequence (i.e. the –VHWK epitope) can be used as a diagnostic tool.

Hence, in a tenth aspect, there is provided SEQ ID No:3, or a variant or fragment thereof, for use as a biomarker for detecting or diagnosing a neurodegenerative disorder.

Preferably, SEQ ID No:3, or a variant or fragment thereof acts as an epitope which may be bound by an antibody or antigen-binding fragment, preferably the antibody or antigen-binding fragment according to the first aspect or third aspect.

Preferably, the variant or fragment of SEQ ID No:3 used as a biomarker comprises or consists of SEQ ID No:6.

The invention also provides a kit for diagnosing patients suffering from neurodegenerative disease.

Hence, according to an eleventh aspect of the invention, there is provided a kit for diagnosing a subject suffering from a neurodegenerative disorder, or a pre-disposition thereto, or for providing a prognosis of the subject's condition, the kit comprising detection means for detecting the concentration of antigen present in a sample from a test subject, wherein the detection means comprises an antibody or antigen-binding fragment thereof according to the first or third aspect, being optionally derivatised, wherein presence of antigen in the sample suggests that the subject suffers from neurodegenerative disorder.

According to a twelfth aspect, there is provided a method for diagnosing a subject suffering from neurodegenerative disorder, or a pre-disposition thereto, or for providing a prognosis of the subject's condition, the method comprising detecting the concentration of antigen present in a sample obtained from a subject, wherein the detection is achieved using an antibody or antigen-binding fragment thereof according to the first or third aspect, being optionally derivatised, and wherein presence of antigen in the sample suggests that the subject suffers from neurodegenerative disorder.

Advantageously, the antibody of the invention may be used to determine if an individual is at a higher risk of developing a neurodegenerative disorder (such as Alzheimer's or Parkinson's) much earlier than is currently possible, so that early treatment can be offered, or information provided to help them make more informed decisions regarding life-style and diet. In addition, early diagnosis of neurodegenerative disorder, or early detection of the risk that a subject may develop a neurodegenerative disorder, would greatly assist a doctor in prescribing medication.

Preferably, the antigen comprises or consists of SEQ ID No: 3, more preferably SEQ ID No:5, and most preferably SEQ ID No:6.

Preferably, the sample comprises a biological sample. The sample may be any material that is obtainable from a subject from which protein is obtainable. The sample may comprise brain, for example Cortical Cortex, Locus Coeruleus or Hippocampus.

FIGS. 18-20 shows that the antibody surprisingly binds to T14 in CSF. Preferably, therefore, the sample comprises cerebrospinal fluid (CSF).

The sample may comprise blood, urine, tissue etc.

FIG. 23 shows that the antibody surprisingly binds to T14 in blood per se. Most preferably, therefore, the sample comprises a blood sample. The blood may be venous or arterial blood.

The kit may comprise a sample collection container for receiving the extracted sample. Blood samples may be assayed for T14 levels immediately. Alternatively, the blood sample may be stored at low temperatures, for example in a fridge or even frozen before the T14 assay is conducted. Detection of T14 may be carried out on whole blood. Preferably, however, the blood sample comprises blood serum. Preferably, the blood sample comprises blood plasma.

The blood may be further processed before the T14 assay is performed. For instance, an anticoagulant, such as citrate (such as sodium citrate), hirudin, heparin, PPACK, or sodium fluoride may be added. Thus, the sample collection container may contain an anticoagulant in order to prevent the blood sample from clotting. Alternatively, the blood sample may be centrifuged or filtered to prepare a plasma or serum fraction, which may be used for analysis. Hence, it is preferred that the T14 is analysed or assayed in a blood plasma or a blood serum sample. It is preferred that T14 concentration is measured in vitro from a blood serum sample or a plasma sample taken from the subject.

Preferably, the kit or method is used to identify the presence or absence of T14-positive cells (i.e. cells comprising SEQ ID No:3 or a variant or fragment thereof) in the sample, or determine the concentration thereof in the sample. The detection means may comprise an assay adapted to detect the presence and/or absence of T14-positive cells in the sample. The kit or method may comprise the use of a positive control and/or a negative control against which the assay may be compared. For example, the kit may comprise a reference for the concentration of T14-positive cells in a sample from an individual who does (i.e. positive control) or does not (i.e. a negative control) suffer from neurodegenerative disorder.

The kit may further comprise a label which may be detected. The term "label" can mean a moiety that can be attached to the antibody, or fragment thereof. Moieties can be used, for example, for therapeutic or diagnostic procedures. Therapeutic labels include, for example, moieties that can be attached to an antibody or fragment thereof of the invention and used to monitor the binding of the antibody to T14 peptide (i.e. SEQ ID No:3) or a fragment thereof, such as SEQ ID No:5 or SEQ ID No: 6. As described herein the antibody or antigen-binding fragment thereof binds specifically to SEQ ID No:3, or a variant or fragment thereof. Preferably, the antibody or antigen-binding fragment thereof does not bind to SEQ ID No:2 (i.e. T30). Preferably, the antibody or antigen-binding fragment thereof does not bind to SEQ ID No:4 (i.e. T15) or Beta-amyloid.

Diagnostic labels include, for example, moieties which can be detected by analytical methods. Analytical methods include, for example, qualitative and quantitative procedures. Qualitative analytical methods include, for example, immunohistochemistry and indirect immunofluorescence. Quantitative analytical methods include, for example, immunoaffinity procedures such as radioimmunoassay, ELISA or FACS analysis. Analytical methods also include both in vitro and in vivo imaging procedures. Specific examples of diagnostic labels that can be detected by analytical means include enzymes, radioisotopes, fluorochromes, chemiluminescent markers, and biotin.

A label can be attached directly to an antibody of the invention, or fragment thereof, or be attached to a secondary binding agent that specifically binds a molecule of the invention. Such a secondary binding agent can be, for example, a secondary antibody. A secondary antibody can be either polyclonal or monoclonal, and of human, rodent or chimeric origin.

The inventors believe that the antibody of the invention may be used as part of a screen for new therapeutic compounds in the drug discovery process. For example, methods and assays to detect the toxic peptide, T14, may be used for candidate compound screening (e.g. HTS and selective library screens, and structure based design), for identifying hits that may offer effective treatment, as well as secondary assays (e.g. in vitro and ex vivo secondary assays), as part of the "hit to lead" development of a pharmaceutical.

Accordingly, in a thirteenth aspect of the invention, there is provided use of the antibody or antigen-binding fragment thereof according to the first or third aspect, in a drug discovery screen, for identifying a therapeutic compound for use in the treatment, prevention or amelioration of a neurodegenerative disorder.

In a fourteenth aspect, there is provided the ex vivo use of a colourimetrically- or to fluorescently-labelled T14 peptide (SEQ ID No: 3), for identifying an agent which inhibits T14 peptide (SEQ ID No: 3) synthesis or activity.

In a fifteenth aspect, there is provided a method for identifying a candidate agent, for use in the treatment, prevention or amelioration of a neurodegenerative disorder, the method comprising the steps of:—

(i) contacting, in vitro or ex vivo, a cell with a test agent, in the presence of the antibody or antigen-binding fragment thereof according to the first or third aspect; and (ii) using the antibody or antigen-binding fragment thereof to detect the presence, concentration or activity of T14 peptide (SEQ ID No: 3), wherein the absence of T14 peptide, or a reduction in T14 peptide synthesis, concentration or activity, as compared to a control, is an indicator that the agent is a candidate for the treatment, prevention of amelioration a disease characterised by inappropriate complement activation.

In a fifteenth aspect, there is provided an assay for identifying an agent that inhibits T14 peptide (SEQ ID No: 3) synthesis or activity, the assay comprising:—
(i) a cell-based expression system;
(ii) the antibody or antigen-binding fragment thereof according to the first or third aspect; and
(iii) a vessel configured to permit contacting of at least one test agent with the expression system.

In a sixteenth aspect, there is provided a method for identifying an agent that modulates T14 peptide (SEQ ID No: 3) synthesis or activity, the method comprising:—
(i) contacting, in vitro or ex vivo, a cell with a test agent, in the presence of the antibody or antigen-binding fragment thereof according to the first or third aspect; and
(ii) using the antibody or antigen-binding fragment thereof to detect the presence, concentration or activity of T14 peptide (SEQ ID No: 3), wherein an alteration in T14 synthesis, concentration or activity, as compared to a control, is an indicator that the test agent modulates T14 peptide (SEQ ID No: 3) synthesis or activity.

It will be appreciated that the antibody or antigen-binding fragment thereof can be used to detect the presence, concentration or activity of the toxic peptide, T14 (SEQ ID No:3) in the assays and methods of the invention. Hence, if the antibody detects T14 or an increase in its concentration or activity in response to the presence of the test compound, then this would indicate that the test compound does not represent a useful candidate as a therapy for treating neurodegenerative disorders. Conversely, if no toxic T14 is detected by the antibody, or it detects a decrease in its concentration or activity in the presence of the test compound, then this would indicate that the test compound is a useful therapeutic for treating neurodegenerative disorders. It is preferred that the methods and assays involve identifying an agent that reduces or prevents the synthesis or activity of the T14 peptide.

Any of the methods described herein may be carried out in vitro or ex vivo. The contacting may be in a substantially cell-free system. Any of the methods may comprise screening an agent that shows a positive indication for the same activity in a cell-based system and/or in vivo in a non-human mammal.

It will be appreciated that the invention extends to any nucleic acid or peptide or variant, derivative or analogue thereof, which comprises or consists of substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the sequence identified as SEQ ID No: 3 (i.e. the T14 polypeptide sequence, or SEQ ID No:6 (i.e. the VHWK epitope), and so on.

Amino acid/polynucleotide/polypeptide sequences with a sequence identity which is greater than 50%, more preferably greater than 65%, 70%, 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90%, 92%, 95%, 97%, 98%, and most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:— (i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. blosum62, pam250, gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. hence, a most preferred method for calculating percentage identity between two sequences comprises (i) preparing a sequence alignment using the clustalw program using a suitable set of parameters, for example, as set out above; and (ii) inserting the values of n and t into the following formula:— sequence identity=(N/T)*100.

Alternative methods for identifying similar sequences will be known to those skilled in the art. For example, a substantially similar nucleotide sequence will be encoded by a sequence which hybridizes to any of the nucleic acid sequences shown herein, or their complements under stringent conditions. By stringent conditions, we mean the nucleotide hybridises to filter-bound DNA or RNA in 3× sodium chloride/sodium citrate (SSC) at approximately 45° c. followed by at least one wash in 0.2× ssc/0.1% SDS at approximately 20-65° c. Alternatively, a substantially similar polypeptide may differ by at least 1, but less than 5, 10, 20, 50 or 100 amino acids from the sequences shown herein.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

Figure 17:
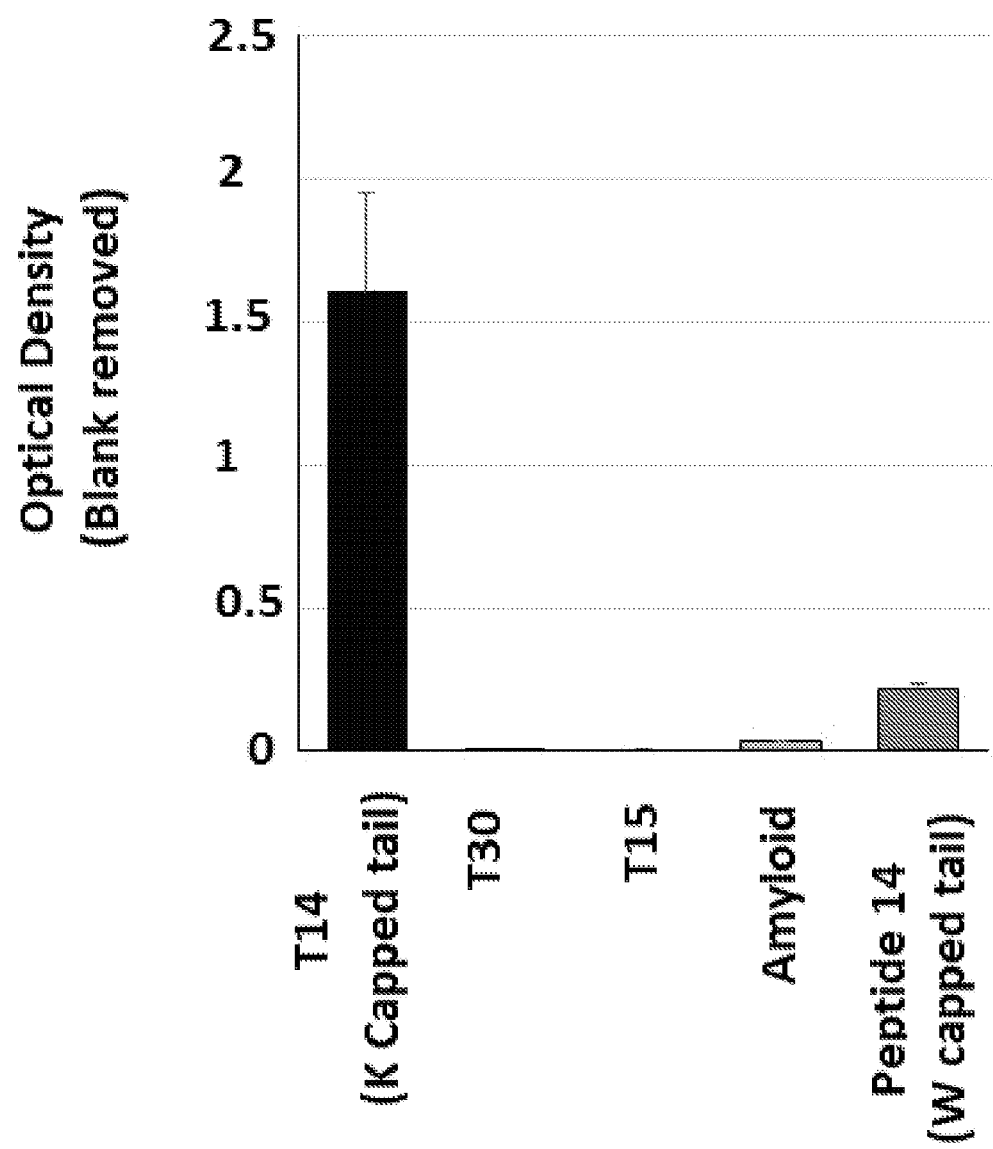
Figure 18:
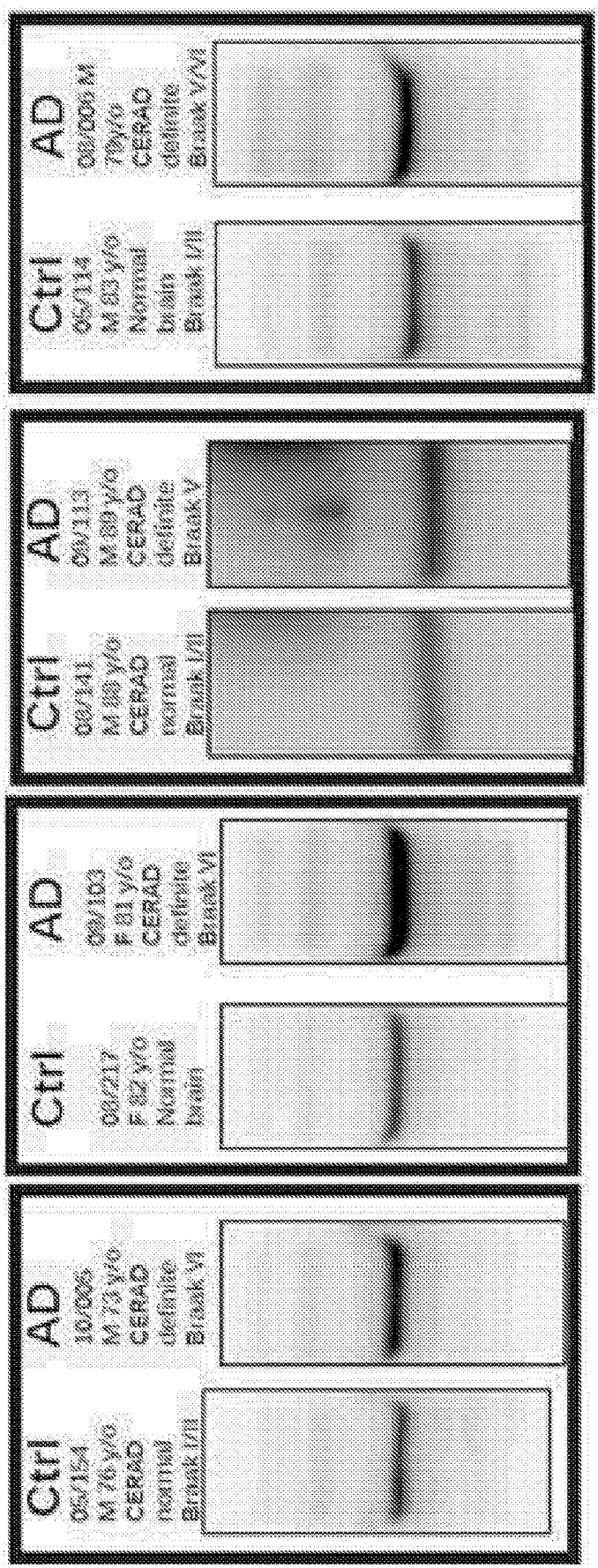
Figure 18:
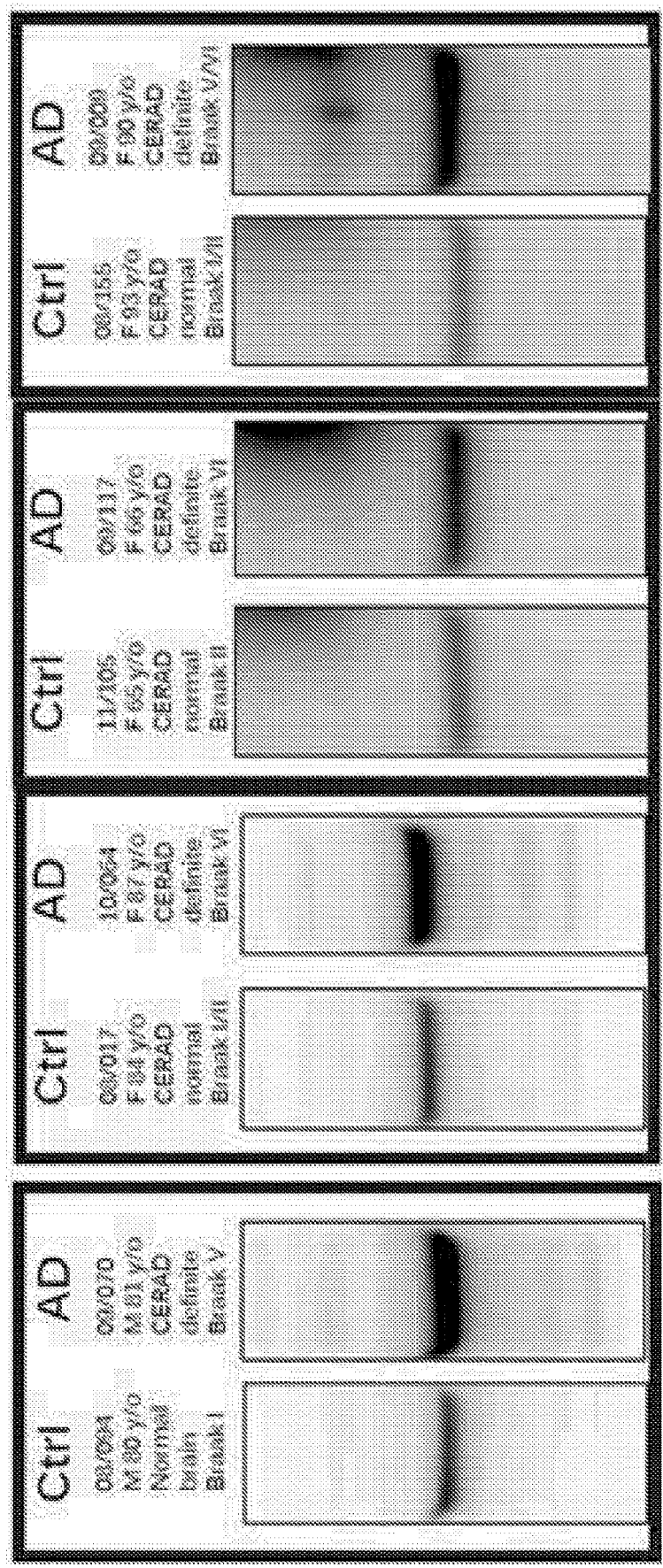
Figure 19:
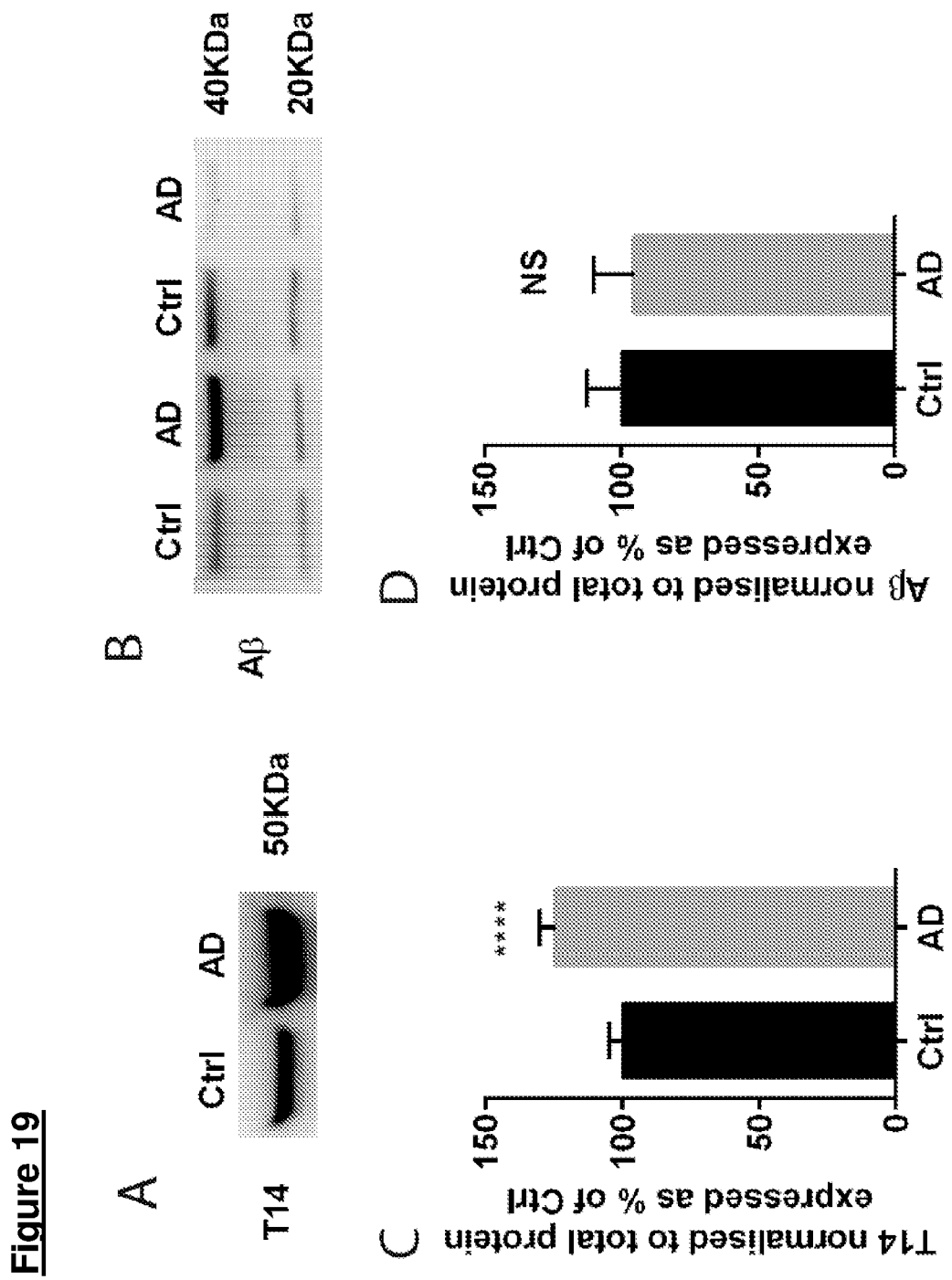
Figure 20:
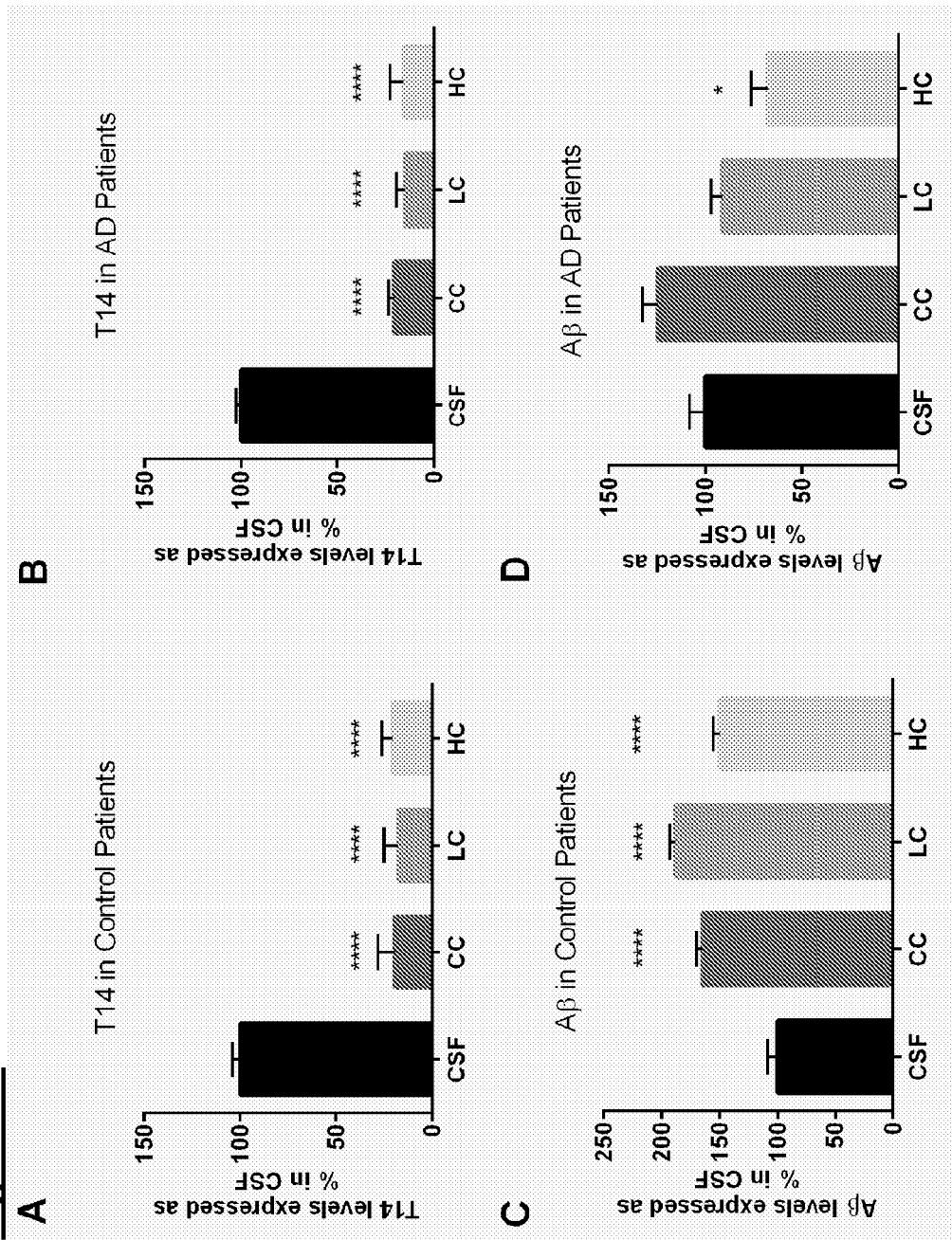
Figure 20:
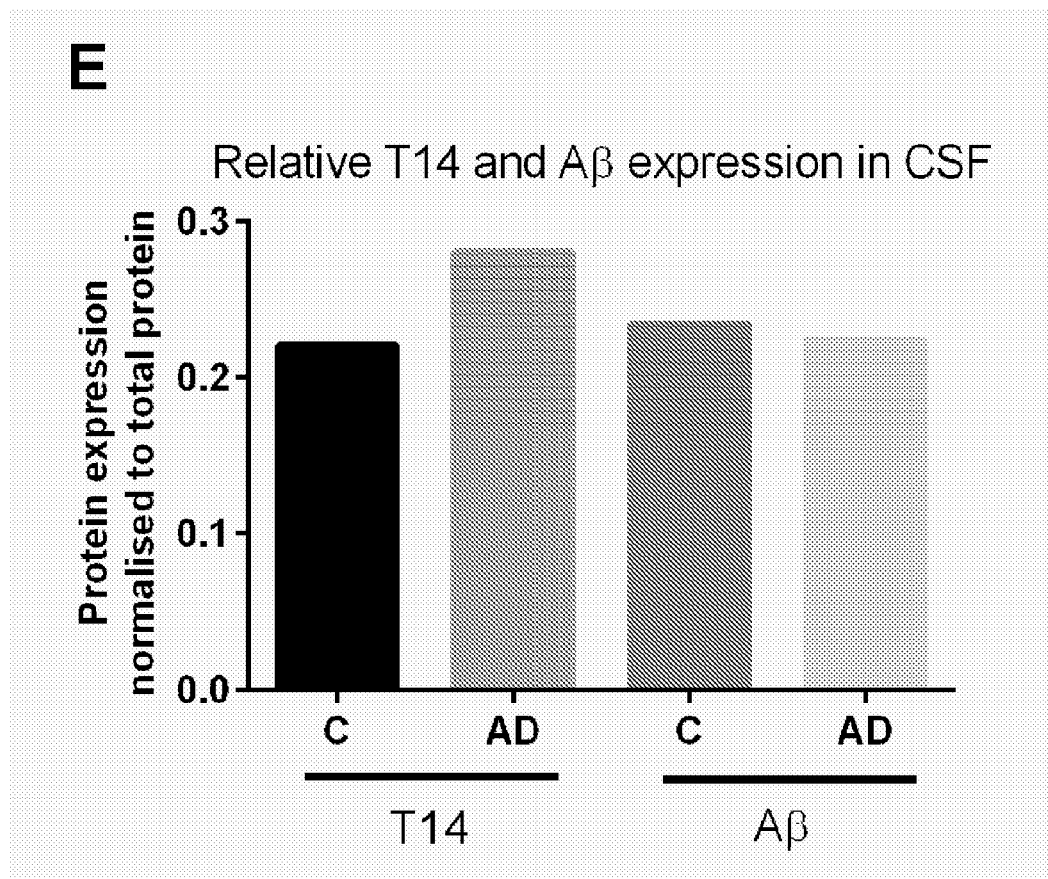
Figure 21:
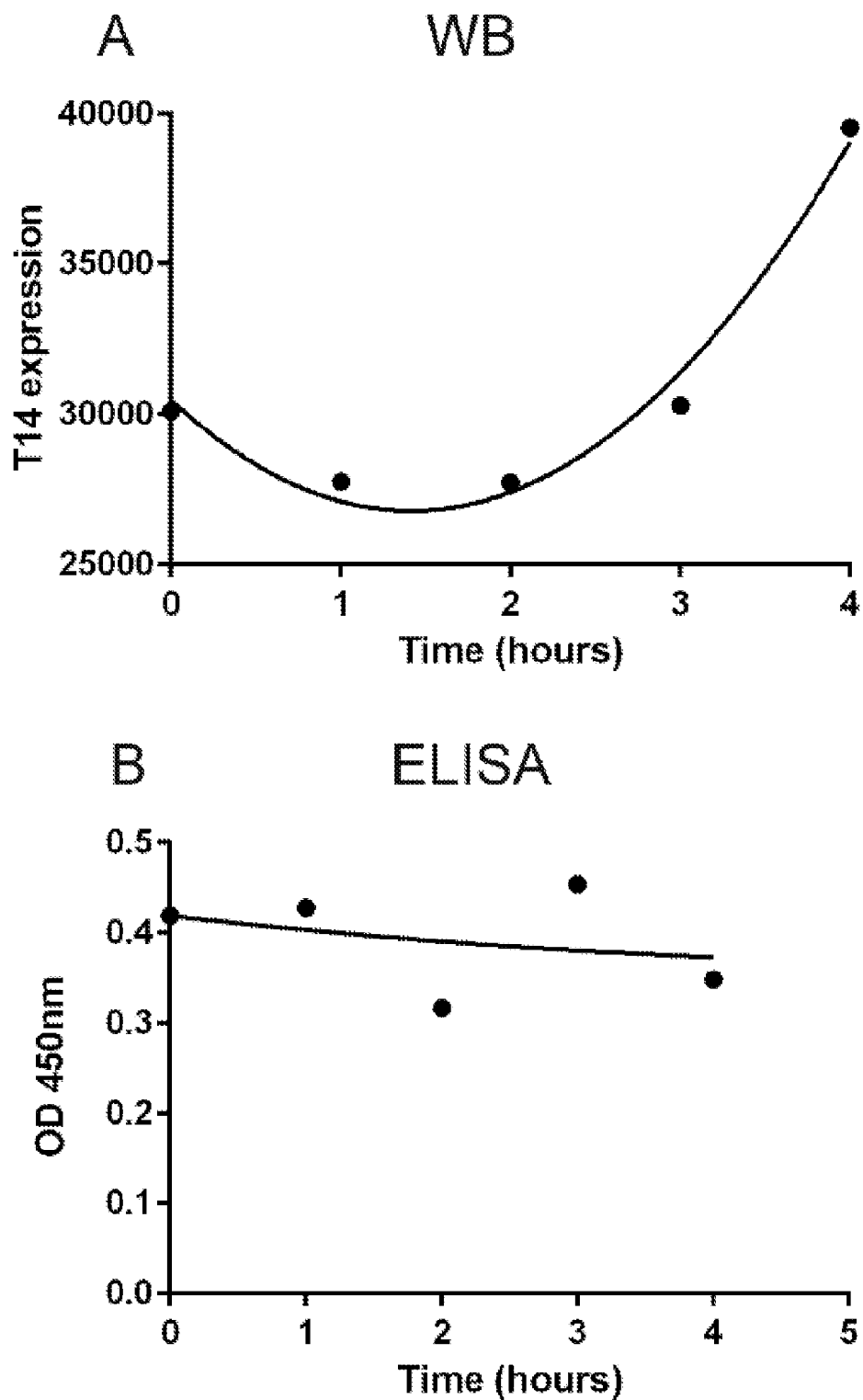
Figure 22:
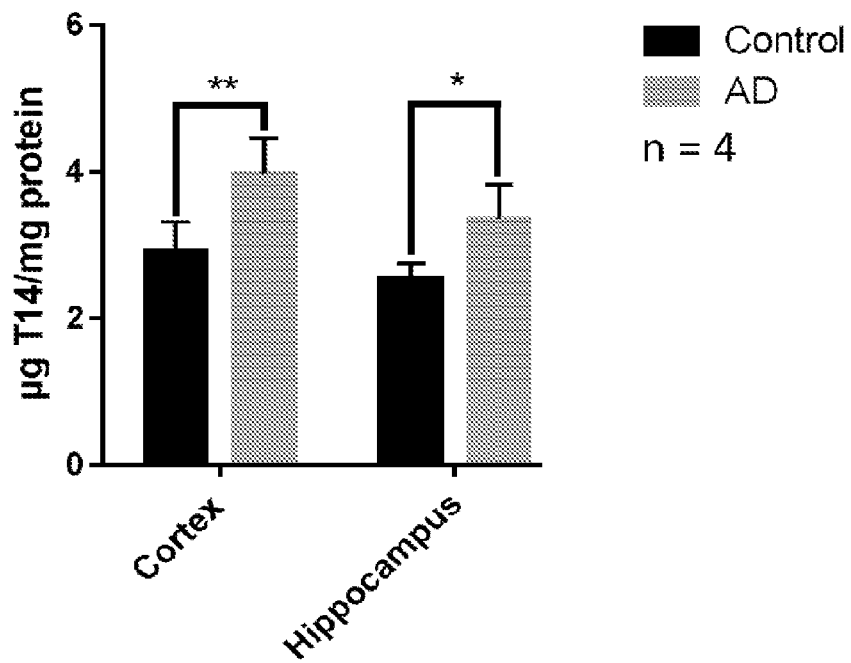
Figure 23:
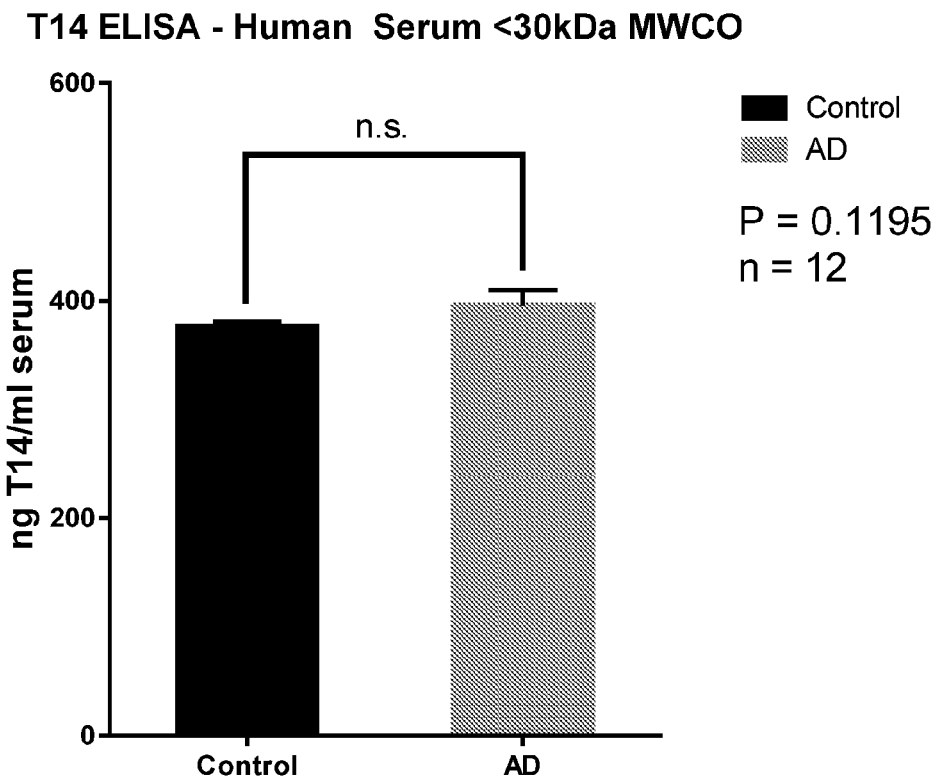
Figure 24:
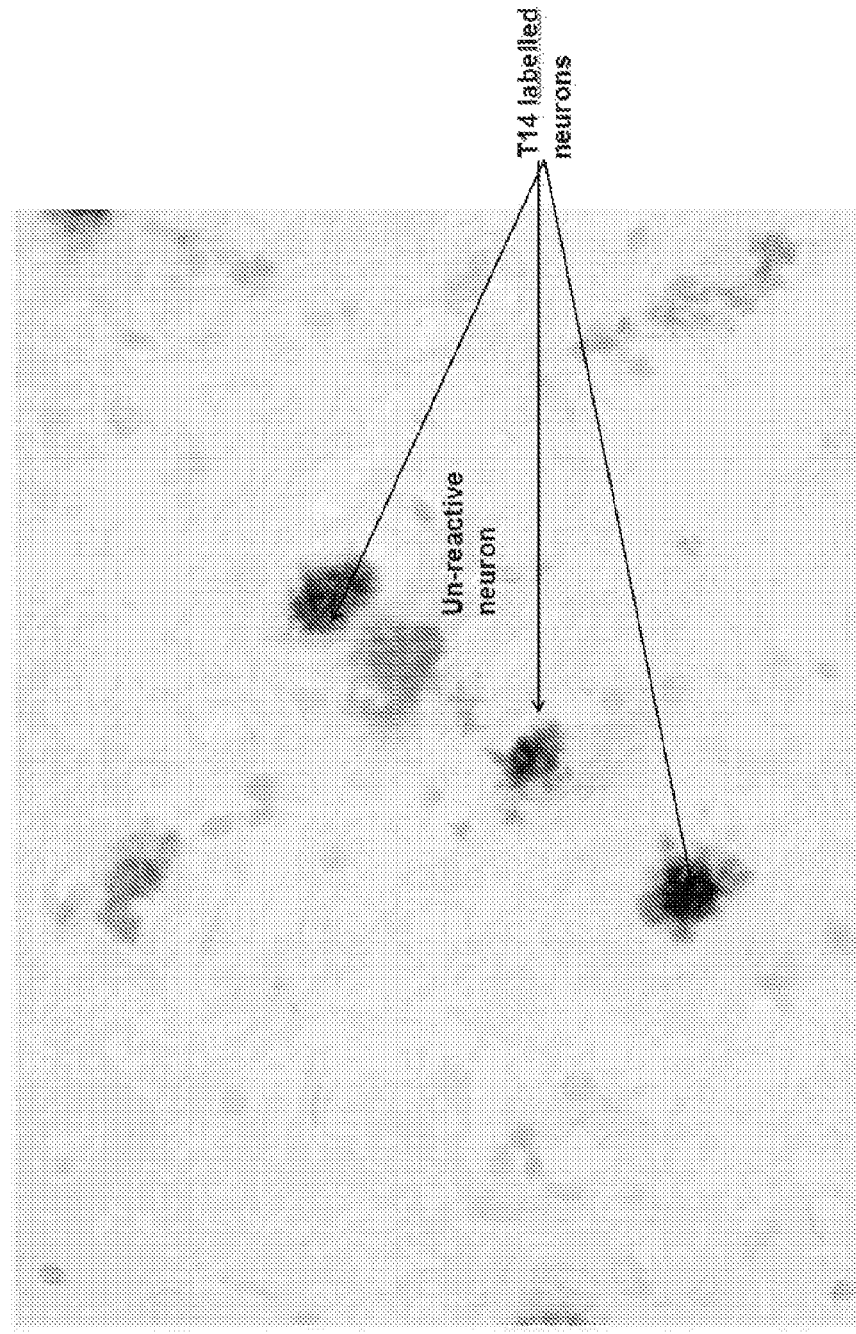
Figure 25:
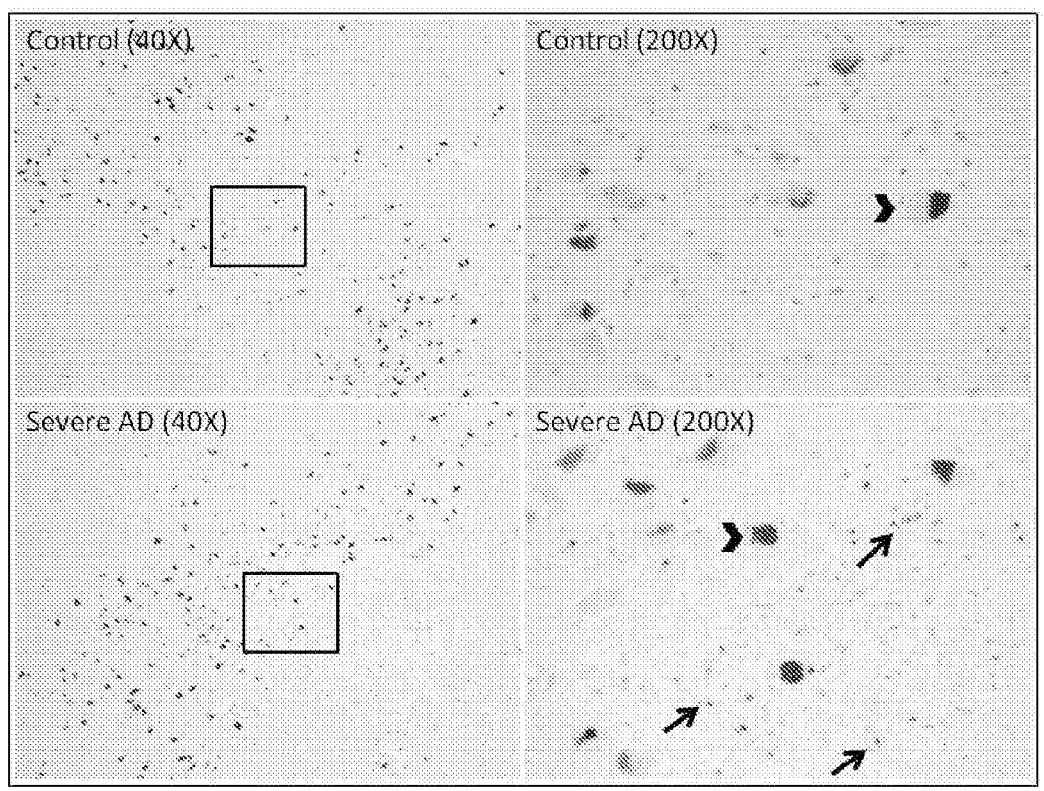

FIG. 17 shows validation of the specificity of the antibody to T14. Histogram shows response to 100 nM exogenous T14, T30, T15, amyloid and T14 without a final K residue added. n=3 in all cases. A clear response to the antibody is only seen with T14;

FIG. 18 shows Western Blot (WB) data for ten age matched pairs of control and AD patients, displaying their patient code, sex, age, CERAD status and Braak stage. T14 levels in CSF increase in the majority (80%) of cases of AD tested using Western Blotting using an embodiment of the antibody of the invention, thus proving the hypothesis and identifying T14 as a biomarker;

FIG. 19 shows T14 levels elevated in CSF in AD patients using an embodiment of the antibody of the invention, but Aβ remain unchanged. FIG. 19(A): T14 expression in post-mortem CSF of Ctrl and AD patients in a representative Western blot. Due to aggregation T14 (Bond, Zimmerman et al. 2009, Cottingham, Hollingshead et al. 2002) is seen with slower electrophoretic mobility (50 KDa) Ctrl: Male, 80 y/o, CERAD normal, Braak I. AD: Male, 81 y/o, CERAD definite, Braak V.; FIG. 19(B): Aβ expression in post-mortem CSF of Ctrl and AD patients in a representative Western blot. Ctrl: Male, 80 y/o, CERAD normal, Braak I. AD: Male, 81 y/o, CERAD definite, Braak V. From left to right: Ctrl: Female, 82 y/o, CERAD normal; AD: Female, 81 y/o, CERAD definite, Braak VI; Ctrl: Male, 83 y/o, CERAD normal, Braak I/II; AD: Male, 79 y/o, CERAD definite, Braak V/VI; FIG. 19(C): Quantification of T14 expression; and FIG. 19(D): Aβ expression in post-mortem CSF of Ctrl (n=10) and AD patients (n=10). T14 levels were normalised to total protein expression as detected by Blot-Faststain™ (Collins et al. 2015) and expressed as percentage of the average of controls +/−SEM. Significant difference at level P<0.0001 indicated by ****;

FIG. 20 shows that T14 levels are consistently higher in CSF in control and AD patients, compared to three brain regions, using an embodiment of the antibody of the invention. However, this is not the case for Aβ. T14 levels were measured in CSF and three brain regions (CC: cerebral cortex, LC: locus coeruleus, HC: hippocampus). Amount of T14 in the brain regions and CSF were expressed % of T14 amount in the CSF in both A) control and B) AD patients. Aβ levels are measured and expressed the same way as above for C) control and D) AD patients. E) The relative amount of T14 and Aβ in CSF (black bars) were then plotted together;

FIG. 21 shows that T14 aggregation grows exponentially with T14 monomer pool remains unchanged. Exogenous T14 stock solution (20 mM) solution was created by resuspension in distilled water. Subsequently, stock solution was diluted to a working stock solution (400 µM) with PBS (pH 10.5). Aggregation was initiated by neutralising the working stock solution by adding PBS (pH 5) to create a final concentration of 200 µM, which was incubated for 0, 1, 2, 3, 4 hours at 25° C. Moreover, T14 monomer control was created by diluting the working stock with PBS (pH 10.5) to 200 µM and incubating at 25° C. for 4 hours. A further no peptide control was created by mixing together pH 5 and pH 10.5 PBS and incubating at 25° C. for 4 hours. WB (A) and ELISA (B) were then conducted on the above T14 aggregation samples and quantified;

FIG. 22 shows that T14 levels in clinical brain tissue (cortex and hippocampus) are significantly elevated (per mg of protein) in the AD brain using an embodiment of the antibody of the invention;

FIG. 23 shows that filtered Human Serum (30 kDa MWCO) shows the presence of T14 to be at detectable levels as measured by the T14 ELISA using an embodiment of the antibody of the invention;

FIG. 24 shows immunohistochemistry results using the antibody showing the present of T14 in global neurons in an advanced Alzheimer's patient; and FIG. 25 shows immunohistochemical staining of human mid-brain with the anti-T14 antibody sections in both non-neurologic control and severe AD.

EXAMPLES

The 'tailed' acetylcholinesterase (T-AChE) is expressed at synapses, and the inventors have previously identified two peptides that could be cleaved from its C-terminus, one referred to as "T14" (14 amino acids long), within the other which is known as "T30" (30 amino acids long), and which both have strong sequence homology to the comparable region of β-amyloid. A further peptide referred to as "T15" corresponds to the last 15 amino acid residues of T30.

The amino acid sequence of the linear peptide, T14, is AEFHRWSSYMVHWK [SEQ ID No: 3].

The amino acid sequence of the linear peptide, T30, is KAEFHRWSSYMVHWKNQFDHYSKQDRCSDL [SEQ ID No: 2]. The amino acid sequence of the linear peptide, T15, which corresponds to the last 15 amino acid residues of T30 is NQFDHYSKQDRCSDL [SEQ ID No: 5].

The AChE C-terminal peptide "T14'" has been identified as being the salient part of the AChE molecule responsible for its range of non-hydrolytic actions. The synthetic 14 amino acids peptide analogue (i.e. "T14"), and subsequently the larger, more stable, and more potent amino acid sequence in which it is embedded (i.e. "T30") display actions comparable to those reported for 'non-cholinergic' AChE.

The inventors have also previously prepared a 14 amino acid long cyclic T14 peptide (i.e. "NBP-14"), which is based on the amino acid sequence of T14, i.e. AEFHRWSSYMVHWK [SEQ ID No:3], but has been cyclated via the terminal Alanine (A) and Lysine (K) residues. Cyclisation can be achieved by several different means. For example, Genosphere Biotechnologies (France) performed the cyclisation of T14 by transforming the linear peptide into an N-terminal to C-terminal lactam. Cyclisation of T14 to create cyclic NBP14 brings together both ends, i.e. HWK-AEF. The inventors have previously shown that cyclic NBP-14 selectively inhibits the non-classical effects of AChE (i.e. the effects of AChE that are independent of its enzymatic activity) and/or its terminal peptide in vitro, and can be used to treat neurodegenerative disorders. NBP14 acts on the α7 nicotinic-receptor to protect cells from linear T14, T30 and β-amyloid toxicity. It also blocks compensatory AChE release induced by the toxicity of linear T14 and T30. In addition, when given alone, cyclic NBP14 has no significant effect on $Ca^{2+}$ concentrations in rat brain slices, but blocks the effects of T30.

Based on their earlier work, the inventors have now developed an antibody which binds with very high specificity to the AChE C-terminal peptide "T14". The have shown that the antibody can be used with high confidence as a diagnostic tool for diagnosing neurodegenerative disorder. They also believe that the antibody can be used in therapy.

Materials and Methods
Synthesis of Polyclonal Antibody
The antibody (deposited on Jan. 30, 2020, with the American Type Culture Collection under Accession No. PTA-126567) was synthesised on order by Genosphere Biotechnologies (Paris, France). Two New Zealand rabbits were used with four immunizations with KLH-peptide ("Pep4":T14-hapten CAEFHRWSSYMVHWK—SEQ ID No. 7) as immunogen over 70 days. The animals were bled four times and the bleeds were pooled. The antiserum was then passed through a gravity column with covalently bound peptide-support, following washing, the antibodies were eluted in acidic

| Manufacturer ELISA Results: Absorbance 405 nm | | | | |
|---|---|---|---|---|
| Antibody | Rabbit No. 1 | | Rabbit No. 2 | |
| Dilution | Pre-immune | Purified | Pre-immune | Purified |
| 1:1 000 | 0.120 | 1.64 | 0.143 | 1.66 |
| 1:10 000 | 0.045 | 0.77 | 0.036 | 0.74 |
| 1:100 000 | 0.016 | 0.19 | 0.017 | 0.19 | buffer and the solution neutralized. Further dialysis against PBS buffer and lyophilisation completed the process.

Optimisation of the T14 Antibody Conditions

The manufacturer's report on the antibody was used to perform the experiments of ELISA at the optimum conditions. In the report, the manufacturer specifies the optical density related to the concentration of antibody (see table below) and the ELISA protocol used for this procedure (see protocol below).

Protocol from the Manufacturer:

Antigens were coated on EIA strips at 10 ug per well. Wells were washed with 200 ul PBS buffer.

Antisera was diluted in series, added in separate wells, and incubated for 2 hours. Unbound antibodies were washed and anti-rabbit IgG-HRP conjugate was added. Plates were washed and colour development run for 15 minutes with TMB substrate. Absorbance was read at 405 nm (2.00 AUFS). Colour intensity was directly proportional to the amount of antibodies. Antibody was positive if absorbance was >2 folds over that of pre-immune serum. Background absorbance for pre-immune serum could reach 0.1 to 0.3.

Conclusion:

For all the experiments described herein, the 1:1000 was the chosen dilution of antibody.

Detection of Peptide in Sample by Using Antibody (ELISA)

The procedure for the ELISA assay was the following:

The standard curves and the samples were run in triplicate. For the detection of T14, Pep4, T15 and amyloid, 8 nanomolar concentrations of each were used for the ELISA. On the other hand, for the motif determination experiment, only one concentration of each of the peptide variants was used of 100 nM. For the detection of T14 on rat brain samples, different dilutions of the protein were used. Due to the value of the human homogenate samples, these were used only with a dilution of 1:160. The standard curve for determination of T14 peptide in brain tissue and the brain tissue samples were diluted in PBS buffer. The standard curves ranged from 8 to 100 nM of T14. Briefly, 96-well immunoplates (NUNC) were coated with 100 µl/well of sample or standard T14, covered with parafilm and incubated overnight at 4° C. The following day the sample was removed by flicking the plate over a sink with running water, and 200 µl of the blocking solution containing 2% Bovine Serum Albumin (BSA) in Tris-Buffered Saline and Tween 20 (TBS-T) was added and incubated for 4 h at room temperature. Blocking solution was then removed and 100 µl of antibody, diluted in blocking solution to 1 µg/ml, was added and incubated overnight at 4° C. The primary antibody was removed the next day and wells were washed 3 times with 200 µl of TBS-T. After, 100 µl of secondary antibody diluted in blocking solution to 0.1 g/ml was added and incubated for 2 h at room temperature; the plate was covered with parafilm during all incubations. After 2 h, the plate was washed 4 times with TBS-T. The addition of 3,3,5,5-tetramethylbenzidine started the colour reaction. The reaction was stopped 15-30 min later with stopping solution containing 2M $H_2SO_4$, and the absorbance was measured at 450 nm in a Vmax plate reader (Molecular devices, Wokingham, UK).

Ellman Assay for AChE Activity

AChE activity was measured using the Ellman reagent that measures the presence of thiol groups as a result of AChE activity. In the case of the G4 experiment, AChE (G4) was assayed alone or in combination with NBP-14 or in combination with Galanthamine. Cells were plated the day before the experiment as for the cell viability assay. Cells were treated with different concentrations of NBP-14 (0.1-100 µM) and T30, T14 and Aβ 10 µM alone or combined with NBP-14 (0.1 and 0.7 µM). After treatment, supernatant (perfusate) of each treatment was collected and 25 µL of each condition were added to a new flat bottomed 96 well plate followed by the addition of 175 µl of Ellman reagent (Solution A: KH2PO4 139 mM and K2HPO4 79.66 mM, pH 7.0; solution B (substrate): Acetylthiocholine Iodide 11.5 mM; Solution C (Reagent): 5,5'-Dithiobis (2-nitrobenzoic acid) 8 mM and NaHCO3 15 mM). The Ellman reagent was prepared as a mixture of the 3 solutions in a ratio 33(A):3(B):4(C). Absorbance measurements were taken at regular intervals (3, 10, 30 and 60 mins) across experiments at 405 nm.

Preparation of Brain Homogenates (Rat and Human)

The samples were prepared as follows. The brain sample was weighed before being placed in a dounce and 1.5 µL of PBS was added per 1 mg of brain material. The brain sample in the bottom of the dounce was homogenised by plunging all the way to the bottom of the dounce using the "Loose" plunger at least 10 times. The "tight" plunger was used to further homogenise the material, ensuring a minimum of 10 full plunges. The homogenised sample was collected in 2 mL Eppendorfs and centrifuged for 15 minutes at 13,000 g in a centrifuge refrigerated at 4° C. Once the centrifugation was finished, the supernatant was collected into prepared 0.5 ml 30 KDa MWCO filters. The samples were centrifuged for 30 minutes at 13,000 g and protease inhibitor cocktail (Roche complete PIC 04693116001) was added to the filtrate. This was used for the ELISA for T14 peptide. The unfiltered sample retentate (>30 kDa) was collected by reversing the filter into a separate microcentrifuge tube and was used to determine the concentration of protein of the initial sample using the Pierce assay (as described below).

Protein Determination

The Thermo Scientific Pierce 660 nm Protein Assay is a ready-to-use, detergent- and reducing agent-compatible assay reagent to quickly measure (A660 nm) total protein concentration compared to a protein standard of bovine serum albumin. For the assay, 10 microliters of each human brain homogenate sample diluted 1:10 in PBS were added to a microtiter 96 well-plate followed by the addition of 150 microliters of Pierce assay. After 5 minutes incubation, the absorbance was measured at 660 nm in a Vmax plate reader (Molecular devices, Wokingham, UK) and the results of optical density were extrapolated to the standard curve of BSA to obtain milligrams per microliter.

Analysis of Data

For all the experiments, comparisons between multiple treatment groups and the same control were performed by one-way analysis of variance (ANOVA) and Tukey's post-hoc tests using GraphPAD Instat (GraphPAD software, San Diego, Calif.). These tests compare the means of every treatment to the means of every other treatment; that is, apply simultaneously to the set of all pairwise comparisons and identify where the difference between two means is greater than the standard error would be expected to allow. Statistical significance was taken at a P value <0.05. Graphs were plotted using Microsoft Excel.

For the human brain experiments, the analysis of data was represented in the figures as the average of the values of 5 control and 7 Alzheimer's patients, and the standard error of the mean applying the Bessel's correction (n−1). In order to convert optical density readings to micrograms of T14 in each sample, a calibration curve was used where different, known concentrations of exogenous T14 was plotted against the respective reading using an 'exponential model'. Finally values were standardised with respect to the content of T14 related to total protein (µg/mg).

Source of Brain Samples

Rats: Fresh homogenised whole brain from male Wistar rats, aged 35 days, from Charles River. Human: Midbrain sections from deep-frozen tissue supplied by the Thomas Willis Oxford Brain Collection (c/o Professor Margaret Esiri). An ethics application was approved by the Human Tissue Bank of the Oxford Radcliffe Hospital NHS that complied with the Human Tissue Act, Human Tissue Authority Codes of Practise and other law relevant to post mortem examinations and use of tissue. Specifically, a coronal slice of about 5 mm with the peri-aqueductal grey above and the cerebral peduncles and substantia nigra below containing the dorsal raphe, the red nucleus and the third nerve nucleus.

Western Blotting

Brain Sample Preparation

Cerebral cortex, Locus Coeruleus, Hippocampus and CSF sections from ten post-mortem AD patients and their age matched controls were kindly donated by Prof. Margaret Esiri and Dr Gabriele DeLuca from the John Radcliffe Hospital Brain Bank, Oxford. Each brain sample was weighed and placed into a douce. For every 1 µg of brain material, 20l of PBS (1×) containing mini EDTA free protease inhibitor cocktail (Roche complete PIC 04693116001) was added to the douce and the homogenisation was carried out using first a "loose" plunger followed by a "tight" plunger. Subsequently, the samples were spun at 13,000 g for 30 minutes at 4° C. and the supernatants were taken. No preparations were required for the CSF samples. All samples were stored at −80° C.

Measuring Protein Sample Concentration

Protein concentrations from the above samples were measured using the Pierce™ 660 nm Protein Assay (Thermo Scientific). In short, a serial dilution (o to 2 mg/ml) was made from a 10 mg/ml stock of bovine serum albumin (BSA). Three replicates of each BSA concentration were prepared by transferring 10 µl of the protein into a clear 96 well plate (Greiner). Then, samples were diluted with three concentrations (1:1, 1:2, 1:10) and three replicates of each concentration were placed into the same 96 well plate with each replicate containing 10 µl of sample. Subsequently, 150 µl of Pearce Reagent was added to the standards and all samples and the mixture was left to incubate for 5 min with gentle shaking. Finally, the plate was read on a spectrophotometer (Molecular Devices) at 660 nm. The protein concentrations of the samples were determined using the slope and y-intercept from the BSA standard curve, both calculated via Microsoft Excel.

Polyacrylamide Gel Electrophoresis of Protein Samples

Polyacrylamide gels (mini-PROTEAN® TGX stain Free™ gels, BIO-RAD) were placed into the electrophoresis tank (BIO-RAD, mini-PROTEAN tetra system) and Running buffer (25 mM TRIS-base, pH 8.6, 192 mM glycine, 0.1% SDS) was added the gel and tank reservoirs (BioRad). Protein samples were prepared by mixing with distilled water and 4× Laemmli sample buffer (final concentrations: 69.5 mM TRIS-HCl pH 6.8, 1.1% LDS, 11.1% (w/v) glycerol, 0.005% bromophenol blue, BIO-RAD) and 2.5% mercaptoethanol (BIO-RAD). Sample equivalent concentration of exogenous T14 was also prepared, which acted as the positive control for measuring endogenous T14 peptide. The mixtures were heated at 95° C. for 5 min before cooling on ice. Samples and the positive control were loaded into the gels and were electrophoresed alongside with a molecular weight marker (Precision Plus Protein™ Dual Xtra Standards, BIO-RAD) at 35 mV for 90 min. Ice block was placed inside the running tank to prevent any overheating.

Transfer of Protein Samples onto PVDF Membrane

Stacking gels were trimmed off and the separating gels were transferred onto PVDF Transfer Membrane (Thermo Scientific) in a Mini Transblot Cell (BIO-RAD). Briefly, the PVDF Transfer Membrane was activated by soaking with methanol for 1 min followed by soaking with distilled water for 2 min. All layers were subsequently saturated with transfer buffer (20 mM TRIS-base pH 8.6, 154 mM glycine, 0.8% w/v SDS and 20% methanol). The transfer sandwich, in the order of bottom to top, consists of transfer sponge, blotting paper, the gel, PVDF Transfer Membrane, blotting paper, transfer sponge were placed into a transfer cassette, which was inserted into the Mini Transblot Cell filled with Transfer Buffer. Finally, electrophoretic transfer took place for 90 min at 200 mA. Ice block was placed inside the transfer tank to prevent any overheating.

Staining of PVDF Membrane

BLOT-Faststain™ (G-Biosciences, USA) was used to stain for total protein, acting as the loading control (Colins et al 2015). Immediate after electrophoretic transfer, the PVDF transfer membrane was stained with the diluted BLOT-Faststain™ fixer solution (10 fold) for 2 min with gentle shaking. The membrane was then incubated with the diluted BLOT-Faststain™ developer solution (4 fold) for 1 min with gentle shaking. Subsequently, the membrane was stored at 4° C. in the dark in the developer solution for 30 min to allow protein bands to reach maximum intensity. Finally, the membrane was washed with cold water to eliminate background staining and imaged using the G box (Syngene). The membrane can then be destained using warm deionised water (40-45° C.) and ready for the blocking stage.

Detection of Protein Bands

The PVDF transfer membrane was blocked in TBS (TRIS-buffered saline, 20 mM TRIS-base pH 7.5, 0.5 mM NaCl) containing 5% skimmed milk powder for 1 h, then washed twice for 7 min each in TTBS (TBS supplemented with 0.05% v/v Tween-20). The membrane was incubated overnight at 4° C. with a primary antibody diluted in TTBS containing 1% skimmed milk powder (Table 1. On the following day, the primary antibody was removed. The membrane was washed three times for 5 min each in TTBS, then incubated for 1 h at room temperature with the secondary antibody. The secondary antibody of choice depends on the type of primary antibody used. It can either be goat anti mouse secondary antibody conjugated to HRP (a9309, Sigma, diluted in TTBS containing 1% skimmed milk powder (working concentration: 1:1000) or goat anti rabbit secondary antibody conjugated to HRP (ab6721, abcam) diluted in TTBS containing 1% skimmed milk powder (working concentration: 1:5000). After secondary antibody incubation, membranes were washed three times for 5 min in TTBS before a final 10 min wash in TBS. Protein bands were detected using the G box (Syngene).

TABLE 1

Primary antibodies used for Western blotting detection.

| Antibody | Species Raised in | Company | Catalogue Number | Working conc. |
|---|---|---|---|---|
| Anti-T14 | Rabbit | Made by Genosphere (the invention) | N/A | 1:1000 |
| Anti-Nicotinic Acetylcholine Receptor alpha 7 | Rabbit | Abcam | Ab10096 | 1:1000 |
| Anti-Phospho-PHF tau | Mouse | Thermo Scientific | MN 1020 | 1:1000 |
| Anti-Amyloid Precursor Protein | Rabbit | Abcam | Ab 2072 | 1:5000 |
| Anti-AChE | Rabbit | Abnova | PAB 5222 | 1:1000 |

Protein Band Imaging and Data Analysis

The PVDF membrane was placed in the G box (Syngene). The focus and zoom settings were adjusted to ensure that the membrane was at its largest at the centre of the screen. Luminol and Peroxide solutions from Clarity™ Western ECL substrate (BIO-Rad) were mixed the equal parts and applied to the membrane. Images were taken in the dark at 1 min time intervals for 5 min to obtain the optimal signal for the protein bands. Following that, the membrane was exposed in white light using an automatic setting in order to obtain an image for the molecular ladder. The blot images were then analysed using image J. Box of equal sizes were placed around protein bands in each lane, allowing measurement of protein band intensities. The background was then subtracted from the band intensities and the results were analysed in Microsoft Excel and the Graphpad software.

Antibody Stripping for Reprobing

The protein signal from the PVDF transfer membrane can be stripped and reprobed for a different protein. Briefly, the membrane was washed with mild stripping buffer (200 mM Glycine, 3.5 mM SDS, 1% v/v Tween-20, pH 2.2) twice for 10 min each. Subsequently, the membrane was washed with PBS twice for 10 min each and then washed with TTBS twice for 5 min each. Clarity™ Western ECL substrate (BIO-Rad) was added to the membrane and imaged using the G Box (Syngene) in order to check for residual protein signals. If residual signal was too strong, then the whole stripping process was repeated. Then, the membrane was ready for subsequent blocking stage and primary antibody probing (see above).

Human Serum (HS) Preparation

The HS was taken from a cohort of Control and AD patents provided by Professor Nigel Hooper at the Institute of Molecular and Cellular Biology, University of Leeds. The samples were filtered by Molecular weight cut-off fi (MWCO) filter by Amy Halliday, a former post-doc working as part of Susan Greenfield's team at the department of Pharmacology in The University of Oxford In 2008. The Serum was filtered separated into fractions of >30 kDa, 30-10 kDa, and <10 kDa. For this study the 30-10 kDa, and <10 kDa portions were recombined in equal quantities to give a spectrum of the T14 present in <30 kDa HS.

ELISA for T14 Peptide Antibody

The standard curves and the samples were run in triplicate. The human brain homogenate samples were diluted 1:160, human serum. The standard curve for determination of T14 peptide in tissue samples were diluted in PBS buffer. The standard curve ranged from 8 to 100 nM of T14. Briefly, 96-well immunoplates (NUNC) were coated with 100 μl/well of sample or standard T14, covered with parafilm and incubated overnight at 4° C. The following day the sample was removed by flicking the plate over a sink with running water, and 200 μl of the blocking solution containing 2% bovine serum albumin (BSA) in Tris-buffered saline and Tween 20 (TBS-T) was added and incubated for 4 h at room temperature. Blocking solution was then removed and 100 μl of antibody, diluted in blocking solution to 1 μg/ml, was added and incubated overnight at 4° C. The primary antibody was removed the next day and wells were washed 3 times with 200 μl of TBS-T. After 100 μl of secondary enzyme-conjugated antibody diluted in blocking solution to 0.1 μg/ml was added and incubated for 2 h at room temperature; the plate was covered with parafilm during all incubations. After 2 h, the plate was washed 4 times with TBS-T. The addition of 3,3,5,5-tetramethylbenzidine started the colour reaction. The reaction was stopped 30 min later with stopping solution containing 2 M $H_2SO_4$, and the absorbance was measured at 450 nm in a Vmax plate reader (Molecular Devices, Wokingham, UK) for the brain homogenate, and a VersaMax plate reader (Molecular Devices, Wokingham, UK) for the human serum.

Immunohistochemical Staining of Human and Rat Brain Sections with Antibody Directed Against T14

1. Fix brain samples in 10% formalin.
2. Dehydrate tissue blocks and embed in paraffin wax.
3. Cut 6 μm sections from each paraffin-embedded tissue block.
4. Melt tissue onto each slide by baking at 60 degrees for 20 minutes.
5. Incubate slides in histoclear (3×5 minutes) to melt wax.
6. Hydrate slides using a graded ethanol series (10× dips 100% EToH, 10× dips 100% EToH, 10× dips 100% EToH, 10× dips 90% EToH, 10× dips 70% EToH).
7. Incubate slides in 3% hydrogen peroxide for 30 minutes to quench endogenous peroxidase activity.
8. Autoclave slides in pH9 buffer solution containing EDTA (121 degrees for 10 minutes).
9. Mount slides onto cassettes and fasten into sequenzas.
10. Wash slides with Tris buffered saline containing 0.05% tween 20 (TBS/T) (2×5 minutes).
11. Apply primary anti-T14 antibody for 1 hour.
12. Wash slides with TBS/T (2×5 minutes).
13. Apply secondary antibody conjugated to horse-radish peroxidase for 40 minutes (provided by Dako, catalogue number K5007). The secondary antibody recognises the invariable region of the T14-primary antibody. The secondary antibody is conjugated to horse-radish peroxidase, an enzyme that catalyses the reaction that enables detection of the chromogen attached to the secondary antibody, which is bound to the T14 primary antibody. Therefore, this enables detection of immuno-labelled T14 in the brain sections.
14. Wash slides with TBS/T (2×5 minutes).
15. Apply Impact VIP peroxidase substrate to slides that are led flat, as outlined in manufacturer's instructions for 15 minutes (provided by Vector Laboratories, catalogue number SK-4605).
16. Wash slides with TBS/T (2×5 minutes).
17. Mount slides with DPX mountant.

All incubations were carried out at room temperature unless otherwise stated.

Results

Example 1—Peptide Recognition

The inventors have isolated a polyclonal antibody from rabbit. FIGS. 1-4 show dose-responses with 1:1000 antibody and the specified nanomolar concentrations of the different peptides (i.e. PEP4, T14, T30 and T15).

Figure 1:
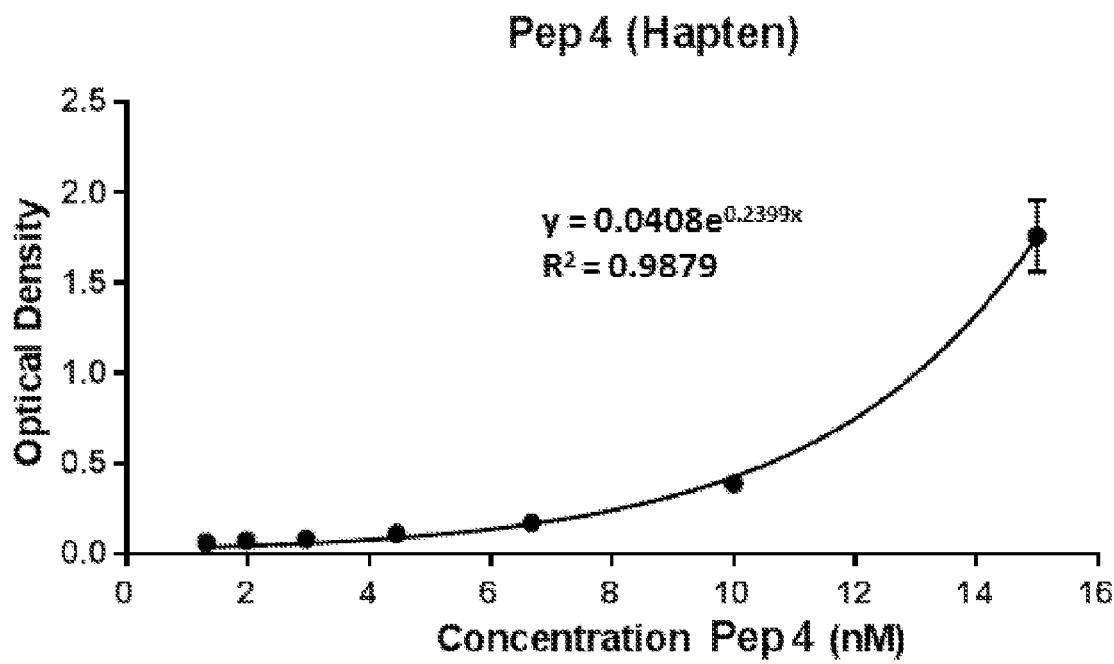
FIG. 1 is a standard curve of Pep4 (SEQ ID No:7) by ELISA.
Figure 2:
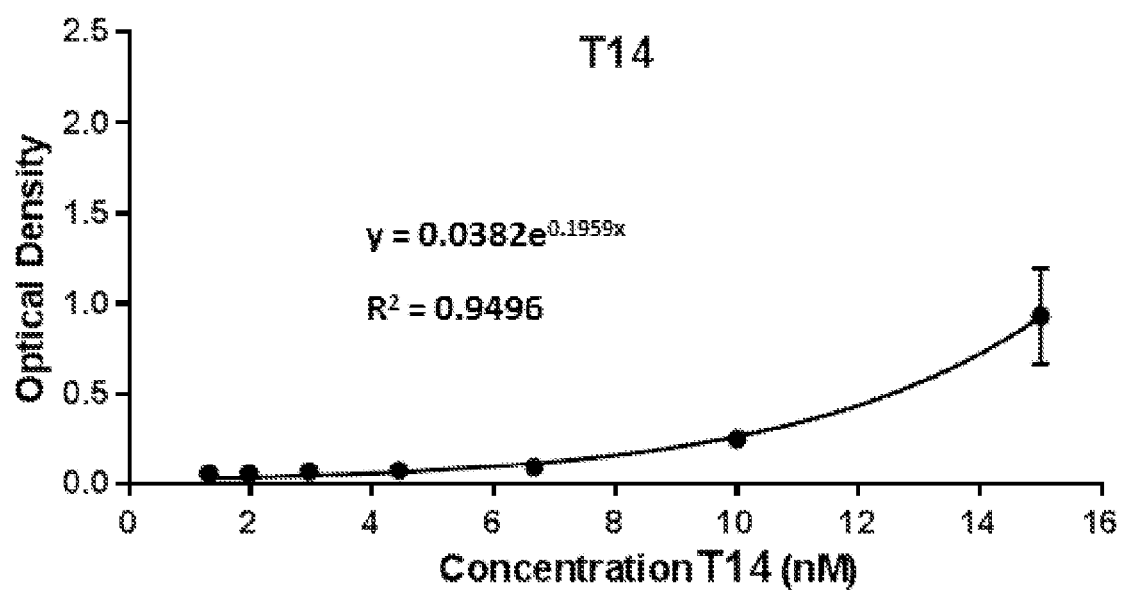
FIG. 2 is a standard curve of T14 (SEQ ID No:3) by ELISA.
Figure 3:
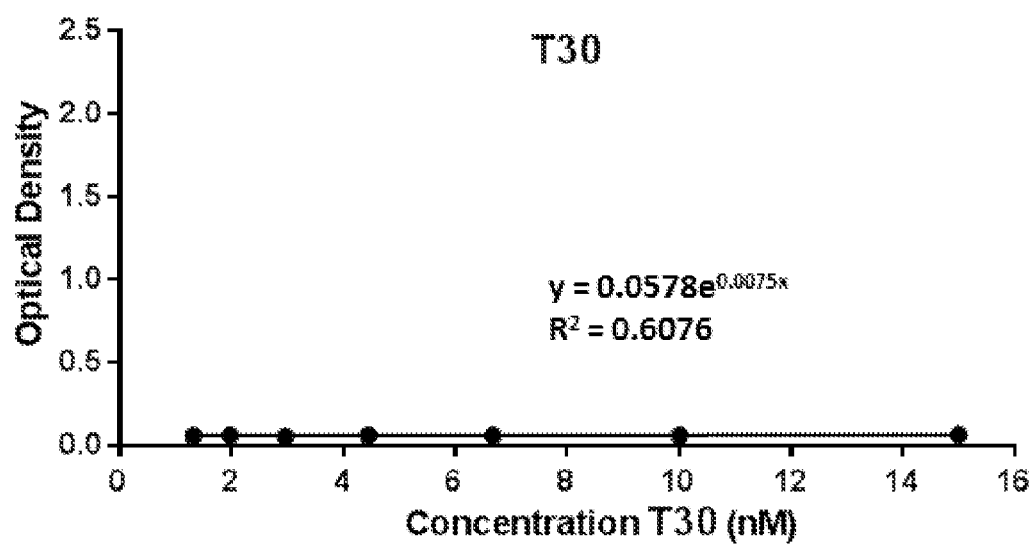
FIG. 3 is a standard curve of T30 (SEQ ID No:2) by ELISA.
Figure 4:
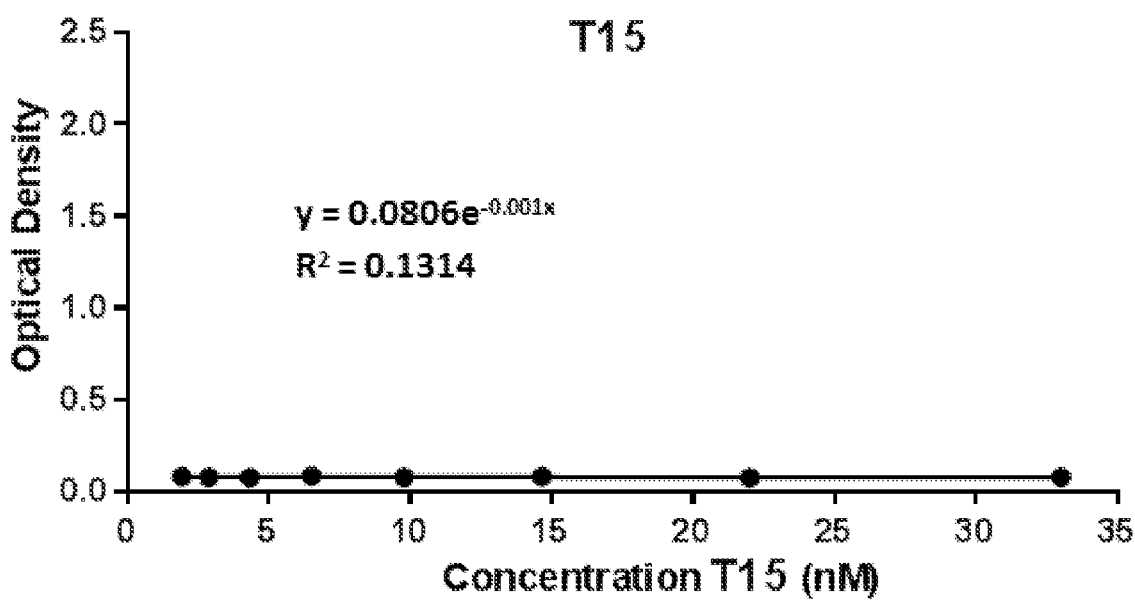
FIG. 4 is a standard curve of T15 (SEQ ID No:4) by ELISA.

As shown in FIG. 1, the antibody specifically detects the anti-peptide used for its synthesis, i.e. PEP4 (CAEFHRWSSYMVHWK—SEQ ID No:7). As shown in FIG. 2, the antibody also specifically binds to T14 (AEFHRWSSYMVHWK—SEQ ID No: 3). However, as shown in FIGS. 3 and 4, the antibody does not bind to T30 (KAEFHRWSSYMVHWKNQFDHYSKQDRCSDL—SEQ ID No:2) or T15 (NQFDHYSKQDRCSDL—SEQ ID No: 5). This means that the requirement for the detection is based on the particular terminal amino acids exposed and the possible tertiary structure they acquire.

In addition, as shown in FIG. 17, the antibody did not recognise amyloid. This means that as mentioned before, recognition by the antibody depends on the different combination of exposed amino acids.

Accordingly, the inventors have demonstrated the surprisingly high specificity of the polyclonal antibody of the invention.

Example 2—Peptide Binding Region

The inventors investigate the immunospecificity of the antibody of the invention by carrying out binding experiments with a series of different linear peptides. The sequences of linear peptides used to determine immunospecificity of the antibody are shown in the Tables 2 and 3.

TABLE 2

Sequences of peptides

| Peptide name | SEQ ID No. | Amino acid sequence | Peptide name | SEQ ID No. | Amino acid sequence |
|---|---|---|---|---|---|
| 909 | SEQ ID No: 10 | WSSYMVHWK | 908 | SEQ ID No: 16 | RWSSYMVHW |
| 1008 | SEQ ID No: 11 | RWSSYMVHWK | 1007 | SEQ ID No: 17 | HRWSSYMVHW |
| 1107 | SEQ ID No: 12 | HRWSSYMVHWK | 1106 | SEQ ID No: 18 | FHRWSSYMVHW |
| 1206 | SEQ ID No: 13 | FHRWSSYMVHWK | 1205 | SEQ ID No: 19 | EFHRWSSYMVHW |
| 1305 | SEQ ID No: 14 | EFHRWSSYMVHWK | 1304 | SEQ ID No: 20 | AEFHRWSSYMVHW |
| 1404 | SEQ ID No: 15 | AEFHRWSSYMVHWK | 1403 | SEQ ID No: 21 | KAEFHRWSSYMVHW |

TABLE 3

Sequences of peptides

| Peptide name | SEQ ID No. | Amino acid sequence | Peptide name | SEQ ID No. | Amino acid sequence |
|---|---|---|---|---|---|
| 1107 | SEQ ID No: 12 | HRWSSYMVHWK | 1209 | SEQ ID No: 27 | WSSYMVHWKAEF |
| 1108 | SEQ ID NO: 22 | RWSSYMVHWKA | 1305 | SEQ ID No: 14 | EFHRWSSYMVHWK |
| 1109 | SEQ ID No: 23 | WSSYMVHWKAE | 1306 | SEQ ID No: 28 | FHRWSSYMVHWKA |
| 1110 | SEQ ID No: 24 | SSYMVHWKAEF | 1308 | SEQ ID No: 29 | RWSSYMVHWKAEF |
| 1206 | SEQ ID No: 13 | FHRWSSYMVHWK | 1404 | SEQ ID No: 15 | AEFHRWSSYMVHWK |
| 1207 | SEQ ID No: 25 | HRWSSYMVHWKA | 1405 | SEQ ID No: 30 | EFHRWSSYMVHWKA |
| 1208 | SEQ ID No: 26 | RWSSYMVHWKAE | 1407 | SEQ ID No: 31 | HRWSSYMVHWKAEF |

Figure 5:
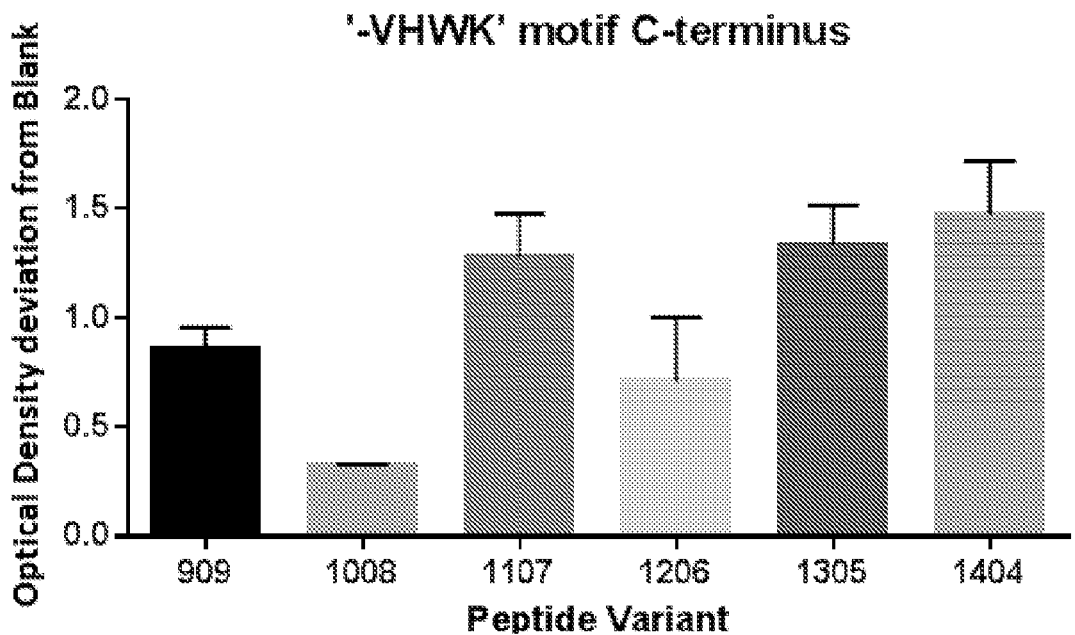
FIG. 5 shows ELISA detection of the 9, 10, 11, 12, 13 and 14 amino acid peptides with the VHWK motif (SEQ ID No:6) at the C-terminus.
Figure 6:
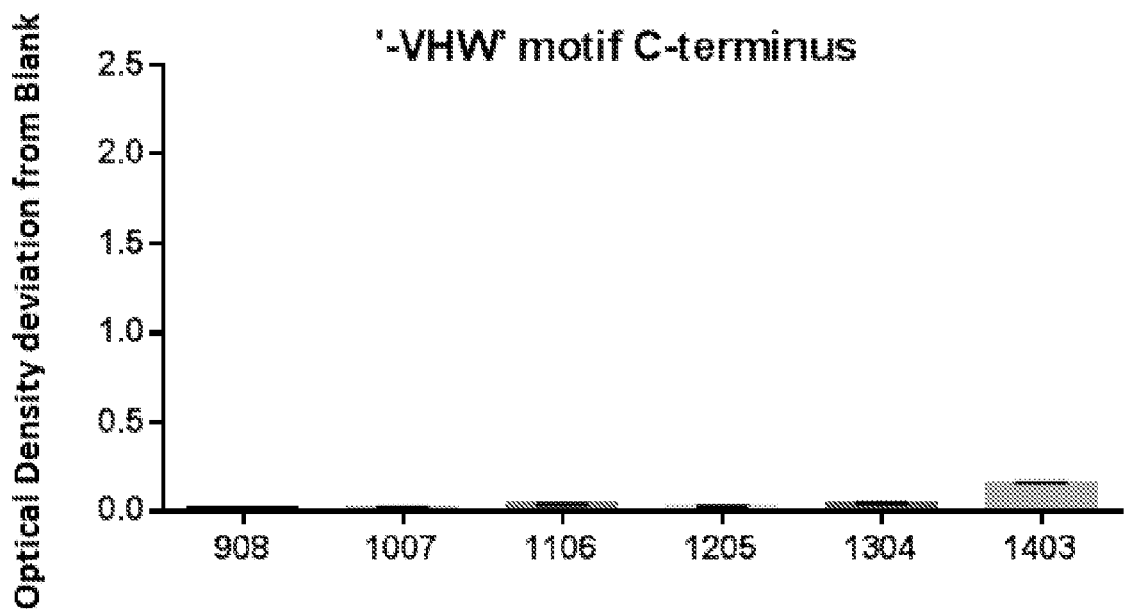
FIG. 6 shows ELISA detection of the 9, 10, 11, 12, 13 and 14 amino acid peptides without the VHWK motif at the C-terminus.
Figure 7:
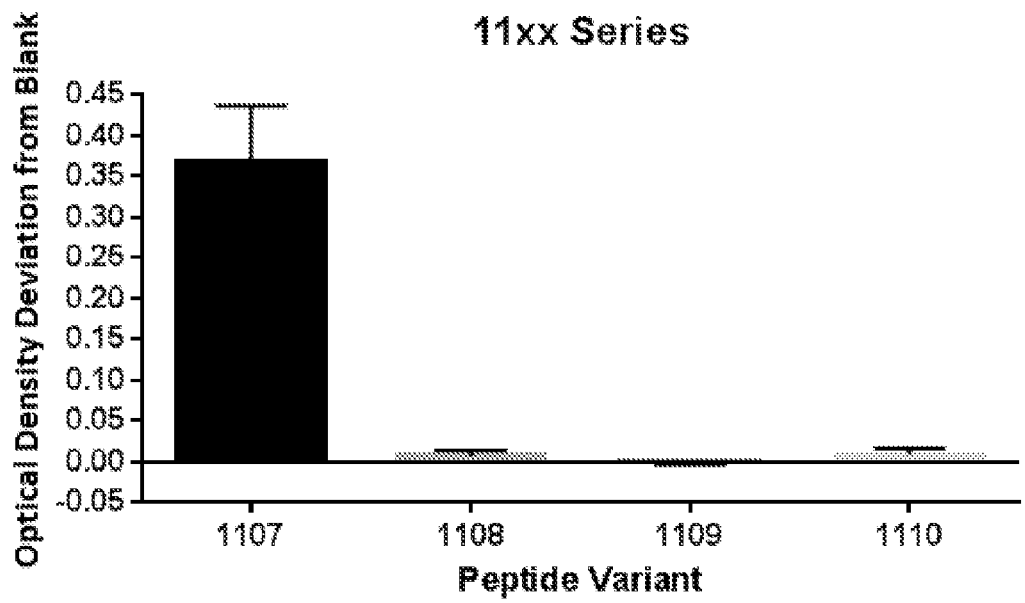
FIG. 7 shows ELISA detection of the 11 amino acid peptides.
Figure 8:
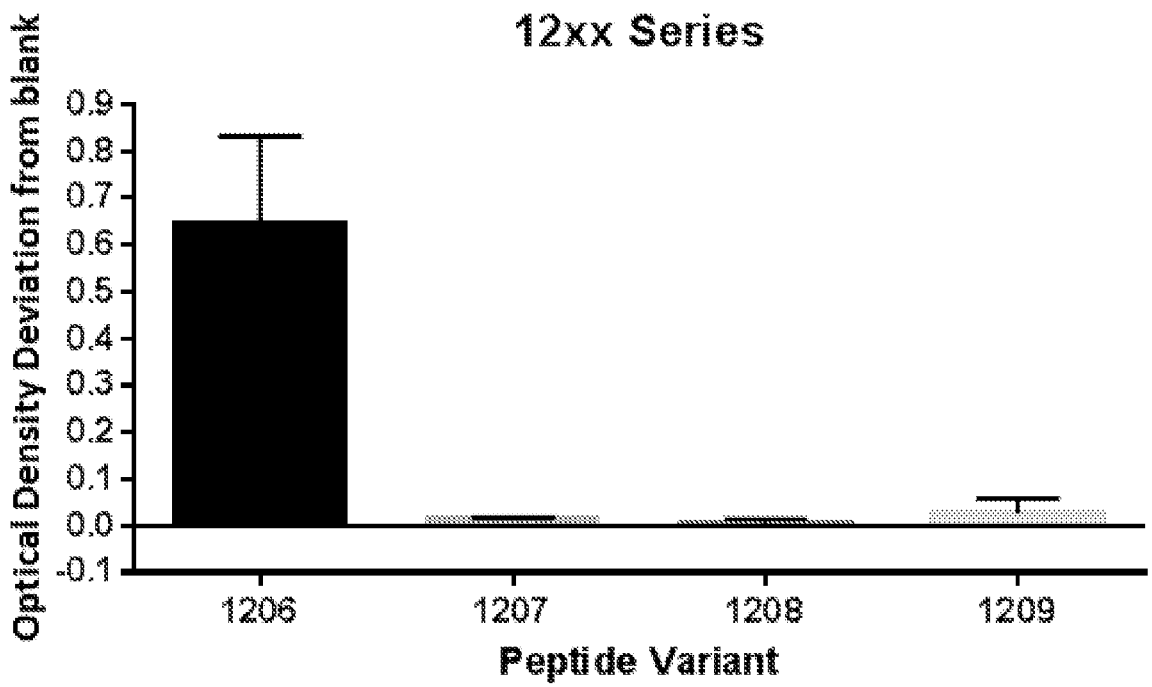
FIG. 8 shows ELISA detection of the 12 amino acid peptides.
Figure 9:
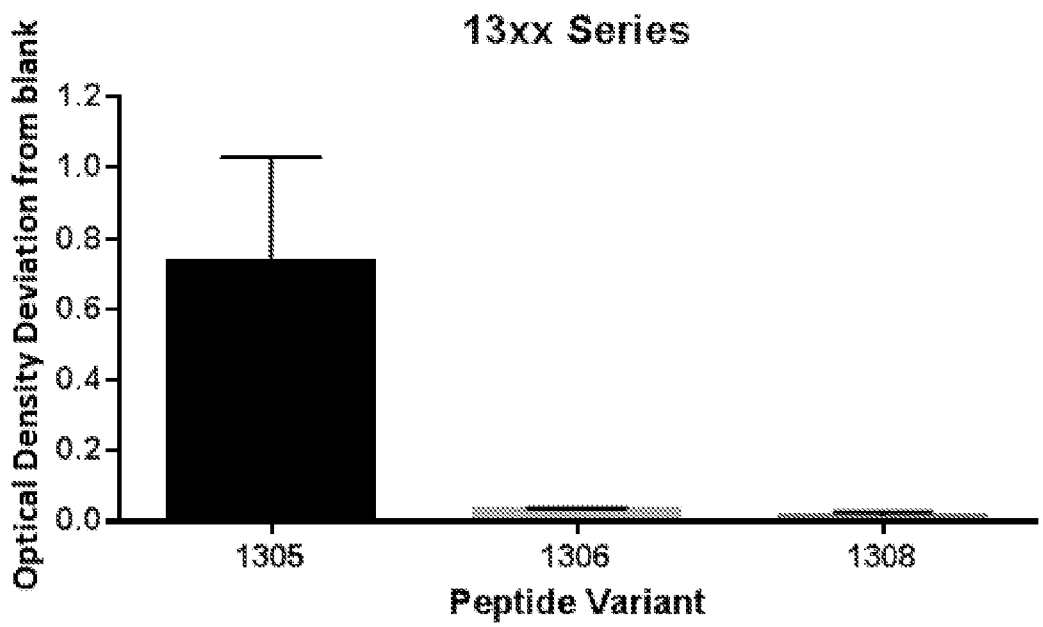
FIG. 9 shows ELISA detection of the 13 amino acid peptides.
Figure 10:
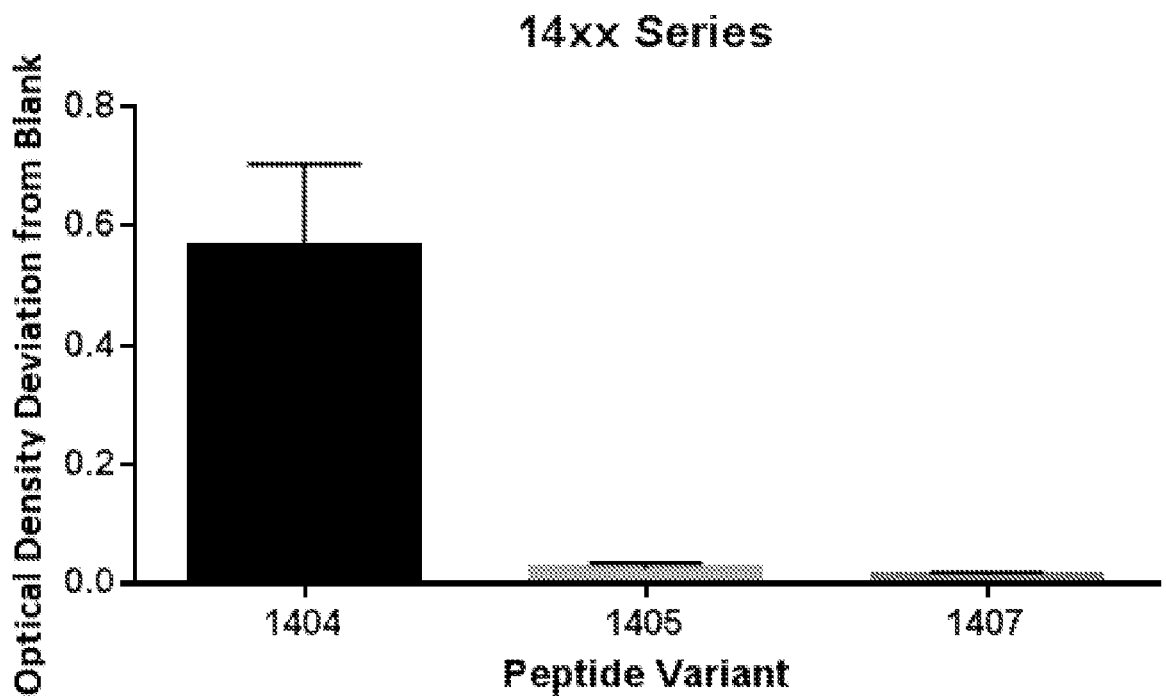
FIG. 10 shows ELISA detection of the 14 amino acid peptides.

As shown in FIG. 5, the antibody specifically requires the presence of a —VHWK amino acid motif or epitope (i.e. SEQ ID No:6) at the C-terminus to be able to detect the peptide. Those peptides that contain the motif, but without the C-terminal K amino acid, are not recognised by the antibody, as shown in FIG. 6. Moreover, those peptides that contain the —VHWK motif, but in which it is not at the end of the sequence, are also not recognised by the antibody as shown in FIG. 6.

FIGS. 7-10 represent binding of the antibody against the different 11, 12, 13, and 14-mer linear peptides, some with the required C-terminal —VHWK motif, and some without it. As can be clearly seen, each of peptides 1107, 1206, 1305 and 1404 all have a C-terminal —VHWK motif to which the antibody strongly binds.

Example 3—AChE Recognition

Figure 11:
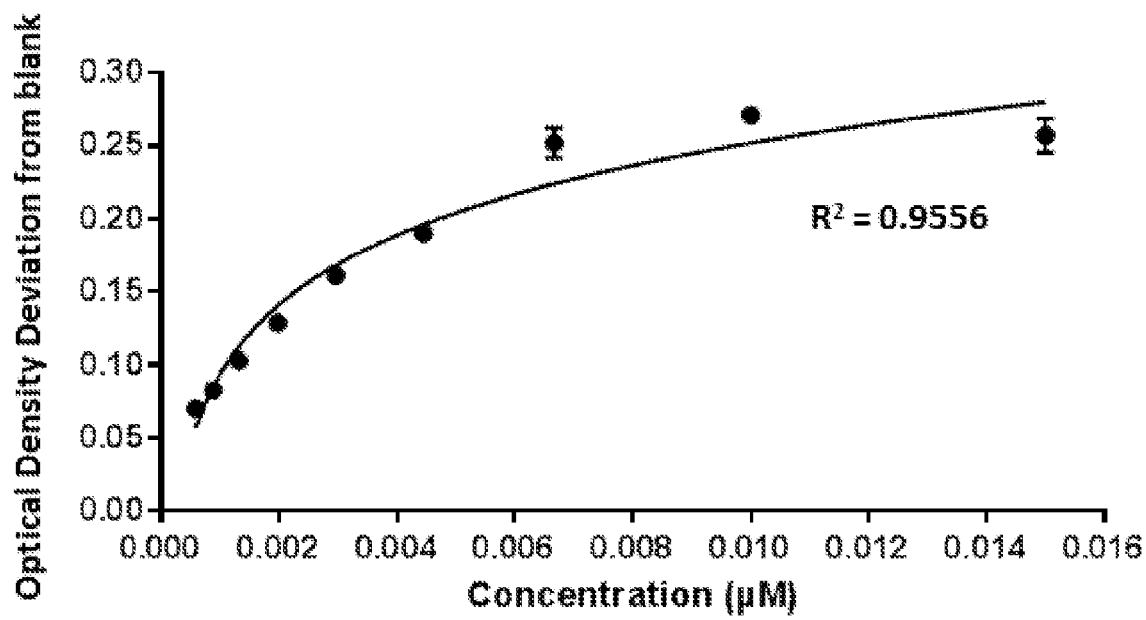
FIG. 11 shows the detection of the AChE molecule by ELISA using one embodiment of the antibody according to the invention.
Figure 12:
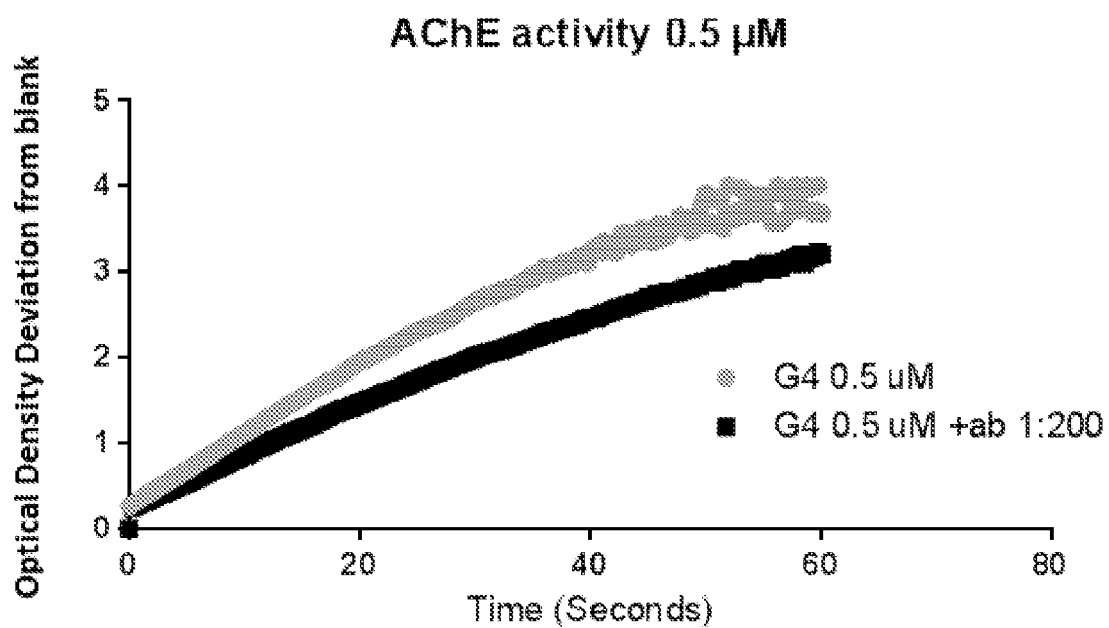
FIG. 12 shows the activity of AChE alone and in combination with one embodiment of the antibody according to the invention determined by Ellman assay.
Figure 13:
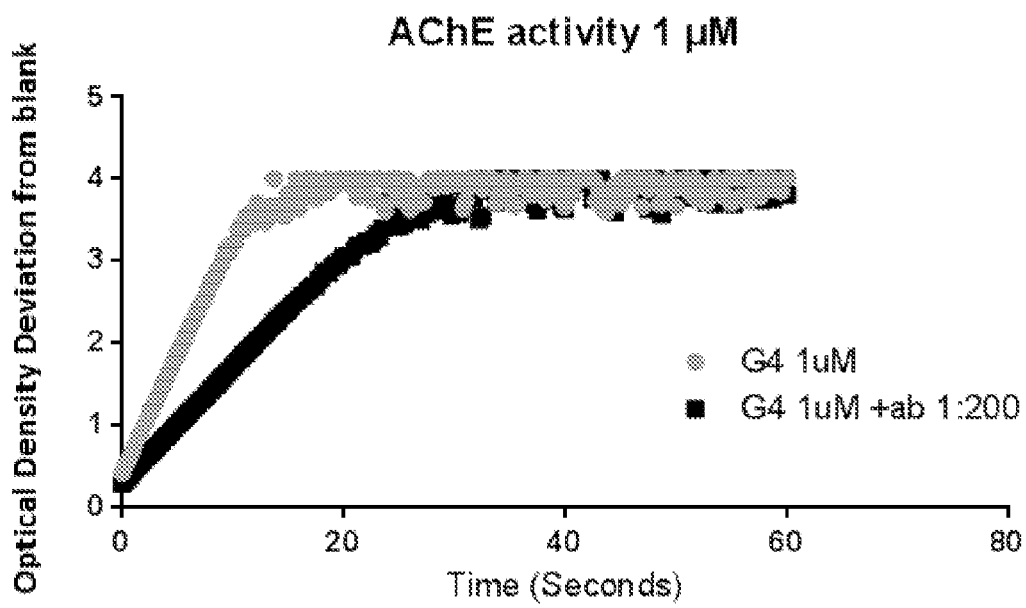
FIG. 13 shows the activity of AChE alone and in combination with one embodiment of the antibody according to the invention determined by Ellman assay.
Figure 14:
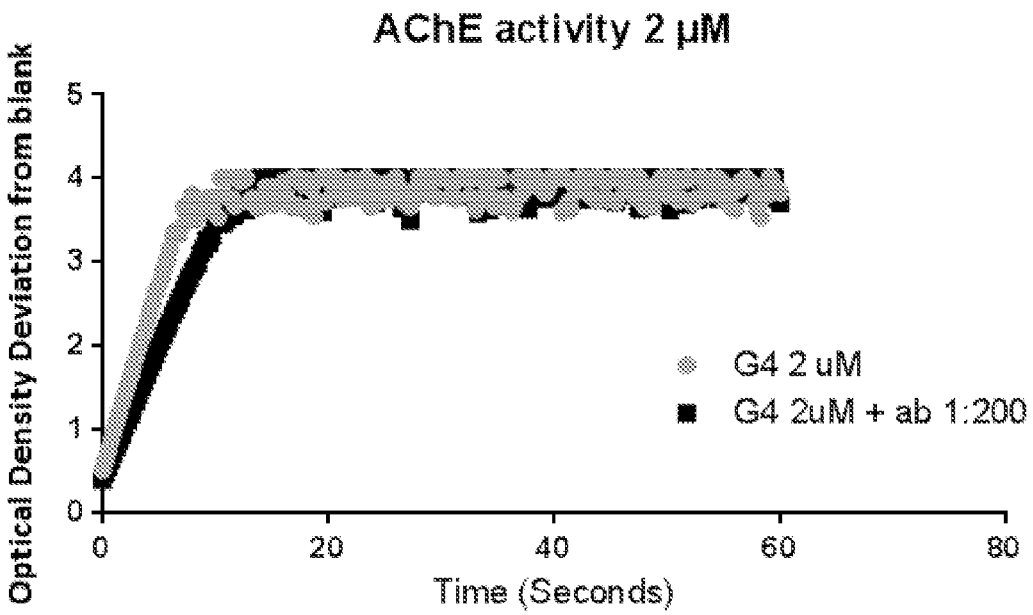
FIG. 14 shows the activity of AChE alone and in combination with one embodiment of the antibody according to the invention determined by Ellman assay.
Figure 15:
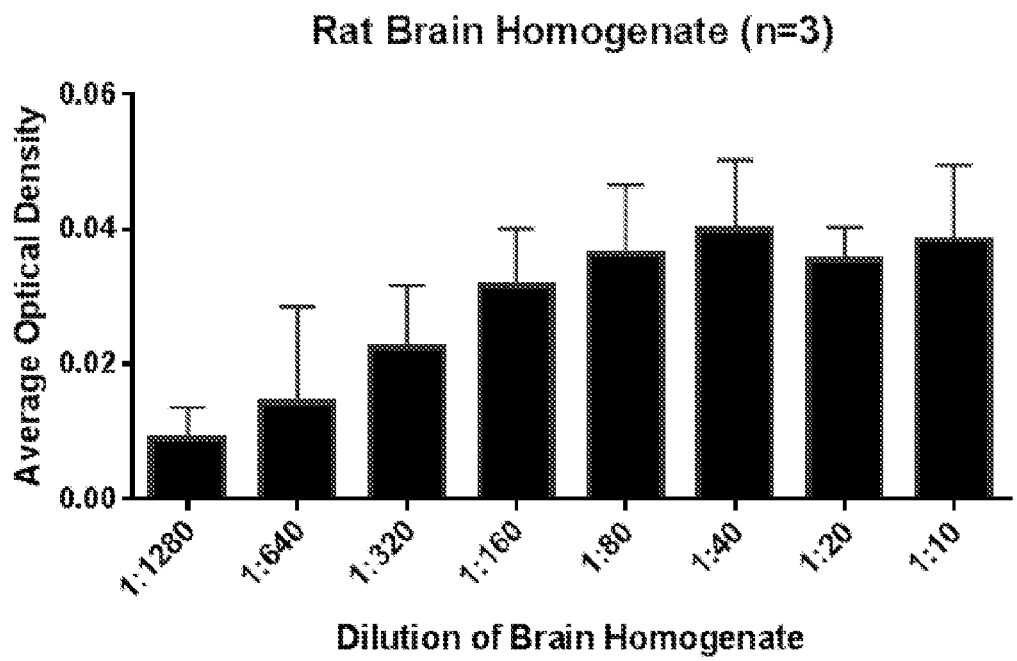
FIG. 15 shows the detection of T14-like peptide in different dilutions of rat homogenate.
Figure 16:
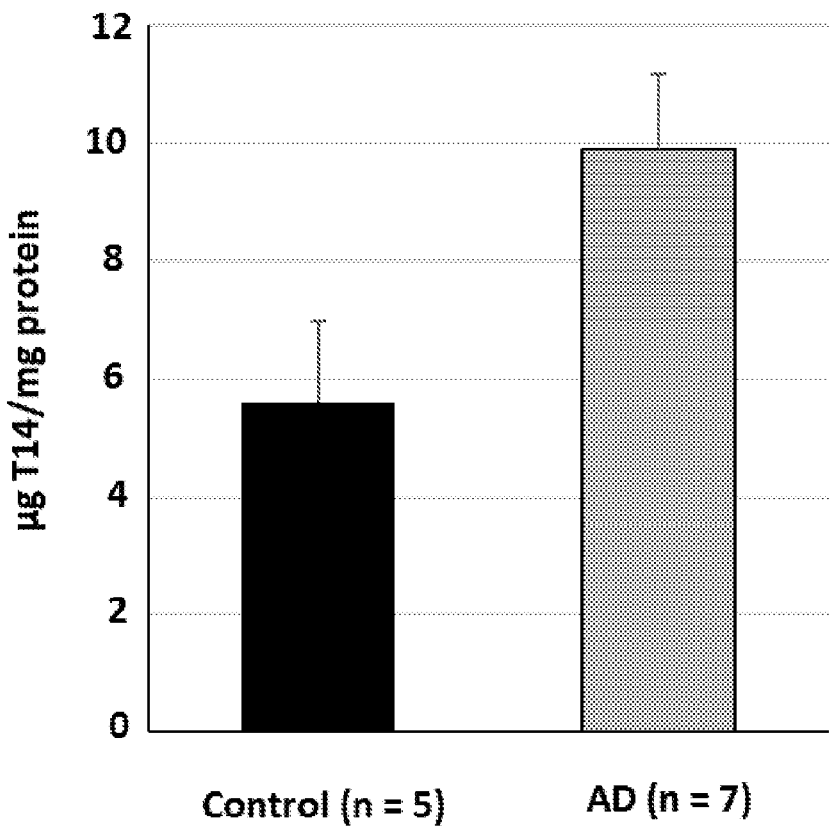
FIG. 16 shows human brain control and AD, expressed as µg T-14 like peptide per mg total protein. The AD samples show a significantly higher concentration at P=0.03.

As shown in FIG. 11, the antibody detects Acetylcholinesterase (AChE, i.e. "G4"), and alters the speed of the hydrolysis of Acetylcholine without affecting the final activity of the enzyme, as shown in FIGS. 12-14, and only significantly when AChE activity is low relative to high concentrations of antibody. Given that AChE activity in the brain and body is very high and that any antibody as therapy would be in the lower dose range, any side effects resulting from compromising enzymatic activity, could be minimised. Moreover, the antibody maximally blocks AChE by approximately 15%, in contrast to Galanthamine, a drug in clinical use, which inhibits activity by much more, i.e. 50% (see WO 2015/004430).

Example 4—Detection in Rat and Human Tissue

When performing the detection with rat and human samples, the samples were filtered with a 30 KDa MWCO filter to remove AChE preventing detection of the enzyme, and a false positive in the sample. The results show how the antibody detects the peptide in both samples. FIG. 15 shows the results in rat brain homogenate, and FIG. 16 shows the results from control and Alzheimer's disease (AD) Human brain homogenate.

Discussion

Specificity of the Antibody

The polyclonal antibody proved to be highly specific to the T14 peptide (crucially, the C-terminal sequence, —VHWK). Its recognition of the full AChE protein suggests that this sequence is exposed and accessible in the tertiary structure. The fact that the antibody did not recognise the linear T30 peptide fragment (within which T14 occurs) is believed to be due to the absence of a lysine (K) at the end of the T30 sequence that is not exposed in the acquired tertiary structure.

Ability to Detect in Complex Samples as Rat and Human Brain

These data show that the antibody is surprisingly viable in biological tissue, even that which has been deep frozen, and that a T14-like peptide exists as an independent biochemical entity, as previously suggested by only indirect evidence (Garcia-Ayllon, M. S. et al. Altered levels of acetylcholinesterase in Alzheimer plasma. *PloS one* 5, e8701, doi: 10.1371/journal.pone.0008701 (2010); Arendt, T., Bruckner, M. K., Lange, M. & Bigl, V. Changes in acetylcholinesterase and butyrylcholinesterase in Alzheimer's disease resemble embryonic development—a study of molecular forms. *Neurochemistry international* 21, 381-396 (1992). Most noteworthy of all is that significant differences can be detected in AD compared to control brains.

Importance of the Detected Sequence

These findings suggest that the detectable sequence (i.e. the —VHWK epitope), and especially the exposed K residue at the C-terminus, could be used as a diagnostic tool as well as a target for therapeutic intervention, including possible use of the antibody itself, if bound to a cytotoxic moeity. The latter application may be constrained by the finding that the antibody could reduce the speed of the AChE enzymatic reaction, but catalysis rates for AChE are so high that they could be above threshold, and indeed explain why drugs, such as galanthamine and Aricept, are nonetheless still in clinical use.

Example 5—Detection of T14 in CSF, as Demonstrated by Western Blot (WB)

Using the antibody of the invention, the inventors then compared T14 fibrils and Aβ in Cerebrospinal fluid (CSF). They found that T14 is detected as a 50 KDa band by Western Blotting, since it forms fibrils. This is further evident by exogenous T14 which aggregates over time, as demonstrated by an increase in T14 Western Blot signal (see FIG. 21A).

Referring next to FIG. 18, T14 fibrils in the CSF increase in 8 out of 10 (80%) of AD cases tested so far using Western Blotting. When all 10 cases were pooled, this increase is about 24% in AD patients compared to controls (p<0.0001, see FIG. 19C). Interestingly, when all 10 AD cases were pooled, there were no changes in Aβ levels in CSF between control and AD patients (see FIG. 19D). As can be seen, T14 and Aβ levels are comparable in CSF of control patients. However, surprisingly, T14 levels increase in AD patients while Aβ levels remain unchanged (see FIG. 20D). Therefore, the inventors have clearly shown that T14 in CSF is a better and more robust AD diagnostic biomarker than Aβ, and can be used for early detection of the disease.

The inventors then compared T14 fibrils and Aβ between CSF and 3 brain areas (Cortical Cortex, Locus Coeruleus, and Hippocampus). They have shown that T14 levels are higher in the CSF compared to the 3 brain regions tested for both control and AD patients, suggesting that T14 is released into the CSF and aggregates there (see FIGS. 20A and 20B). In contrast, they observed that Aβ levels are higher in the 3 brain regions (Cortical Cortex, Locus Coeruleus, Hippocampus) compared to CSF for the control patients (see FIG. 20C), and that there is no significant difference in Aβ levels between Cortical Cortex, Locus Coeruleus and CSF for control patients (see FIG. 20D). Also, Aβ levels are lower in hippocampus than CSF for AD patients (see FIG. 20D).

It is clear therefore that amyloid in CSF does not reflect AD as consistently as T14 does. T14 levels are much higher in CSF than in brain tissue, suggesting that T14 is primarily released as a free molecule for long range signalling rather than aggregating, as does amyloid, in brain tissue. Hence, T14 is a much better biomarker than amyloid in AD, and there is clearly potential for T14 as a sensitive indicator for Parkinson's Disease, as well as Alzheimer's disease.

Thus, the antibody of the invention can clearly be used to detect T14 in the brain areas tested, as well as in the CSF, where T14 levels are elevated, and so easier to detect.

Example 6—ELISA Data on T14 Monomers in Brain Samples

Following on from Example 5, the inventors next used the polyclonal antibody specific to the C-terminus of T14 to detect T14 monomers in additional brain samples. They compared T14 levels in the brain Cortex and Hippocampus. The samples were filtered using a 30 kDa MWCO filter to eliminate larger proteins, such as AChE and albumin, thereby reducing background signal.

As shown in FIG. 22, they found that T14 levels are significantly elevated (per mg of protein) in both the Cortex and the Hippocampus of the AD brain in a study comparing 4 age matched pairs of Control and AD patients. The inventors have shown therefore that T14 is increased in brain regions well known to be associated with damage in Alzheimer's Disease.

Example 7—Comparing Levels of T14 in Control and AD Human Serum

Although it is clear, from Examples 5 and 6, that T14 can be readily detected in the brain and CSF using the antibody of the invention, obtaining brain and CSF samples from living patients is a highly invasive and risky exercise. Accordingly, the inventors investigated the potential of using the antibody to detect T14 in human blood serum (HS) samples that have been in −80° C. storage for a long period of time. The aim of the study was to use these samples to optimise the ELISA for use with fresher samples of HS that can be processed. The samples had been filtered using a 30 kDa MWCO filter to eliminate larger proteins, such as AChE and albumin, thereby reducing background signal.

Referring to FIG. 23, the pilot study of 12 age matched pairs of control and AD patient HS revealed that it is surprisingly possible to detect T14 in filtered human serum using the antibody. Furthermore, T14 is elevated in AD when compared with control. The data illustrate therefore that it is possible to detect T14 in HS, and so can be used as a simple non-invasive diagnostic tool, and would be preferable to obtaining CSF (or brain) samples from patients having, or suspected of having, a neurodegenerative disorder.

Example 8—Immunocytochemistry

Referring to FIG. 24, there is shown the first visualisation of T14 present in global neurons in advanced Alzheimer's disease by immunocytochemisty. Since this particular region shown is typically vulnerable in Parkinson's disease, it supports the theory that the two degenerative diseases share a common mechanism, based on toxic T14.

Example 9—Immunohistochemical Staining of Human Mid-Brain Sections with the Anti-T14 Antibody Referring to FIG. 25, there is shown T14 immunostaining of the substantia nigra of the midbrain in a control and severe Alzheimer's disease (AD) sample at 40× and 200× magnifications. The extracellular T14 immunolabeled deposits in severe AD (arrows) are shown, as are the typical dopaminergic neuronal cytoplasmic T14 immunostaining pattern in controls and AD (arrowheads). A range of T14 neuronal cytoplasmic staining patterns is captured in the fields of view. As can be seen in the Figure, T14 is released (arrows) from the cells of the AD sample, but not in the controls. The T14 release or secretion from the AD cells is believed to be due to leakage from dying neurons. The extracellular deposits of T14 appear to coalesce with the dark melanin, i.e. dopamine.

The invention claimed is:

1. A method for diagnosing and treating a subject suffering from Alzheimer's disease, or a pre-disposition thereto, comprising:
   (a) obtaining a sample from the subject;
   (b) contacting the sample with the polyclonal antibody deposited at American Type Culture Collection Patent Deposit Number PTA-126567, or an antigen-binding fragment thereof, that specifically binds to the exposed C-terminal lysine (K) residue of SEQ ID No:3, wherein the antibody or antigen-binding fragment thereof specifically binds to SEQ ID No:6 and wherein the antibody or antigen-binding fragment thereof does not bind to SEQ ID No:2, SEQ ID No:4 and/or SEQ ID No:8;
   (c) detecting the presence of an antigen comprising SEQ ID No:3 in the sample;
   (d) diagnosing the subject with Alzheimer's disease when an increased presence of antigen in the sample is detected compared to one or more control samples; and
   (e) administering an effective amount of a treatment for Alzheimer's disease to the diagnosed subject.

2. A method for evaluating a putative therapeutic compound for use in the treatment or amelioration of Alzheimer's disease, the method comprising:
   contacting a sample comprising the putative therapeutic compound and the polyclonal antibody that is deposited at American Type Culture Collection Patent Deposit Number PTA-126567, or an antigen-binding fragment thereof;
   measuring the presence and/or amount of T14 in the sample by detecting binding of T14 to the antibody or antigen-binding fragment; and
   determining the putative therapeutic compound is useful for the treatment or amelioration of Alzheimer's disease if no T14 is detected by the antibody, or if a decrease in T14 concentration or activity in response to the presence of the putative therapeutic compound is detected compared to one or more controls; or
   determining the putative therapeutic compounds is not useful for the treatment or amelioration of Alzheimer's disease if T14 is detected by the antibody, or if an increase in T14 concentration or activity in response to the presence of the putative therapeutic compound is detected compared to one or more controls.

3. A method for diagnosing and treating a subject suffering from Alzheimer's disease, or a pre-disposition thereto, the method comprising:
   (a) obtaining a sample from the subject;
   (b) contacting the sample with the polyclonal antibody deposited at American Type Culture Collection Patent Deposit Number PTA-126567;
   (c) detecting the presence of an antigen consisting of SEQ ID No: 3 in the sample;
   (d) diagnosing the subject with Alzheimer's disease when the increased presence of antigen in the sample is detected compared to one or more controls; and
   (e) administering an effective amount of a treatment for the Alzheimer's disease to the diagnosed subject.

4. The method according to claim 3, wherein the sample comprises cerebrospinal fluid (CSF).

5. The method according to claim 3, wherein the sample comprises blood, urine or tissue.

6. A method for diagnosing and treating a subject suffering from, or a pre-disposition thereto Alzheimer's disease, the method comprising:
   (a) obtaining a sample from the subject;
   (b) detecting the presence of SEQ ID No: 3 in the sample, wherein detection comprises contacting the sample with the polyclonal antibody deposited at American Type Culture Collection Patent Deposit Number PTA-126567;
   (c) diagnosing the subject with Alzheimer's disease when increased presence of the antibody binding to SEQ ID No: 3 is detected compared to one or more controls; and
   (d) administering an effective amount of a treatment for the Alzheimer's disease to the diagnosed subject.

* * * * *